(12) United States Patent
Hunt

(10) Patent No.: US 11,375,923 B2
(45) Date of Patent: Jul. 5, 2022

(54) SYSTEMS AND METHODS FOR MONITORING WOUND CLOSURE

(71) Applicant: Smith & Nephew PLC, Watford (GB)

(72) Inventor: Allan Kenneth Frazer Grugeon Hunt, Beverley (GB)

(73) Assignee: Smith & Nephew PLC, Watford (GB)

(*) Notice: Subject to any disclaimer, the term of this patent is extended or adjusted under 35 U.S.C. 154(b) by 360 days.

(21) Appl. No.: 16/641,964

(22) PCT Filed: Aug. 17, 2018

(86) PCT No.: PCT/EP2018/072296
§ 371 (c)(1),
(2) Date: Feb. 25, 2020

(87) PCT Pub. No.: WO2019/042790
PCT Pub. Date: Mar. 7, 2019

(65) Prior Publication Data
US 2020/0221976 A1 Jul. 16, 2020

Related U.S. Application Data

(60) Provisional application No. 62/551,646, filed on Aug. 29, 2017.

(51) Int. Cl.
*A61M 1/00* (2006.01)
*A61F 13/00* (2006.01)
(Continued)

(52) U.S. Cl.
CPC ...... *A61B 5/1109* (2013.01); *A61F 13/00068* (2013.01); *A61M 1/90* (2021.05);
(Continued)

(58) Field of Classification Search
CPC ........ A61M 1/00; A61M 13/02; A61M 27/00; A61M 2205/3317; A61M 2205/702;
(Continued)

(56) References Cited

U.S. PATENT DOCUMENTS 3,014,483 A 12/1961 Frank et al.
3,194,239 A 7/1965 Sullivan et al.
(Continued)

FOREIGN PATENT DOCUMENTS

AU 2012261793 B2 11/2014
AU 2013206230 B2 5/2016
(Continued)

OTHER PUBLICATIONS

WordNet 3.0, Farlex clipart collection. © 2003.*
(Continued)

*Primary Examiner* — Tatyana Zalukaeva
*Assistant Examiner* — Ilya Y Treyger
(74) *Attorney, Agent, or Firm* — Knobbe, Martens, Olson & Bear, LLP

(57) ABSTRACT

Embodiments disclosed herein relate to systems, devices and methods for monitoring dimensional changes in medical devices attached to or implanted in the body, such as wound fillers. Disclosed embodiments may facilitate measuring the degree of wound closure by incorporating conductive elements into the wound filler. In some embodiments, the conductive elements may be conductive filler, a flexible conductive element, or an arrangement of discrete non-flexible conductive elements. The density of conductive material in an area or volume of the wound filler upon wound closure may be detected by a detection device that assesses the local dielectric constant of the wound filler, such as through use of a capacitive plate, or by a detection device that measures the resonant frequency of a conductive element.

17 Claims, 13 Drawing Sheets

(51) Int. Cl.
  *A61B 5/11* (2006.01)
  *A61F 13/02* (2006.01)
  *A61M 27/00* (2006.01)
  *A61B 17/50* (2006.01)

(52) U.S. Cl.
  CPC .............. *A61F 2013/00357* (2013.01); *A61M 2205/3317* (2013.01); *A61M 2205/702* (2013.01)

(58) Field of Classification Search
  CPC ................ A61F 13/00; A61F 13/00068; A61F 2013/00357; A61B 17/50
  See application file for complete search history.

(56) References Cited

U.S. PATENT DOCUMENTS

| | | | |
|---|---|---|---|
| 3,578,003 A | 5/1971 | Everett | |
| 3,789,851 A | 2/1974 | Leveen | |
| 3,812,616 A | 5/1974 | Koziol | |
| 4,467,805 A | 8/1984 | Fukuda | |
| 4,608,041 A | 8/1986 | Nielsen | |
| 4,637,819 A | 1/1987 | Ouellette et al. | |
| 4,699,134 A | 10/1987 | Samuelsen | |
| 4,815,468 A | 3/1989 | Annand | |
| 5,176,663 A | 1/1993 | Svedman et al. | |
| 5,264,218 A | 11/1993 | Rogozinski | |
| 5,368,910 A | 11/1994 | Langdon | |
| 5,376,067 A | 12/1994 | Daneshvar | |
| 5,409,472 A | 4/1995 | Rawlings et al. | |
| 5,415,715 A | 5/1995 | Delage et al. | |
| 5,423,857 A | 6/1995 | Rosenman et al. | |
| 5,512,041 A | 4/1996 | Bogart | |
| 5,514,105 A | 5/1996 | Goodman, Jr. et al. | |
| 5,562,107 A | 10/1996 | Lavender et al. | |
| 5,584,859 A | 12/1996 | Brotz | |
| 5,636,643 A | 6/1997 | Argenta et al. | |
| 5,695,777 A | 12/1997 | Donovan et al. | |
| 5,928,210 A | 7/1999 | Ouellette et al. | |
| 6,176,868 B1 | 1/2001 | Detour | |
| 6,291,050 B1 | 9/2001 | Cree et al. | |
| 6,503,208 B1 | 1/2003 | Skovlund | |
| 6,548,727 B1 | 4/2003 | Swenson | |
| 6,566,575 B1 | 5/2003 | Stickels et al. | |
| 6,685,681 B2 | 2/2004 | Lockwood et al. | |
| 6,712,839 B1 | 3/2004 | Lonne | |
| 6,770,794 B2 | 8/2004 | Fleischmann | |
| 6,787,682 B2 | 9/2004 | Gilman | |
| 6,883,531 B1 | 4/2005 | Perttu | |
| 6,977,323 B1 | 12/2005 | Swenson | |
| 7,004,915 B2 | 2/2006 | Boynton et al. | |
| 7,144,390 B1 | 12/2006 | Hannigan et al. | |
| 7,315,183 B2 | 1/2008 | Hinterscher | |
| 7,351,250 B2 | 4/2008 | Zamierowski | |
| 7,361,184 B2 | 4/2008 | Joshi | |
| 7,438,705 B2 | 10/2008 | Karpowicz et al. | |
| 7,494,482 B2 | 2/2009 | Orgill et al. | |
| 7,498,802 B2 * | 3/2009 | Takahata .............. | G01D 5/2066 324/249 |
| 7,615,036 B2 | 11/2009 | Joshi et al. | |
| 7,622,629 B2 | 11/2009 | Aali | |
| 7,625,362 B2 | 12/2009 | Boehringer et al. | |
| 7,683,667 B2 | 3/2010 | Kim | |
| 7,700,819 B2 | 4/2010 | Ambrosio et al. | |
| 7,779,625 B2 | 8/2010 | Joshi et al. | |
| 7,815,616 B2 | 10/2010 | Boehringer et al. | |
| 7,857,806 B2 | 12/2010 | Karpowicz et al. | |
| 7,863,495 B2 | 1/2011 | Aali | |
| 7,892,181 B2 | 2/2011 | Christensen et al. | |
| 7,896,856 B2 | 3/2011 | Petrosenko et al. | |
| 7,909,805 B2 | 3/2011 | Weston | |
| 7,910,789 B2 | 3/2011 | Sinyagin | |
| 7,931,774 B2 | 4/2011 | Hall et al. | |
| 7,942,866 B2 | 5/2011 | Radl et al. | |
| 7,951,124 B2 | 5/2011 | Boehringer et al. | |
| 7,964,766 B2 | 6/2011 | Blott et al. | |
| 7,976,519 B2 | 7/2011 | Bubb et al. | |
| 7,976,524 B2 | 7/2011 | Kudo et al. | |
| 8,030,534 B2 | 10/2011 | Radl et al. | |
| 8,057,447 B2 | 11/2011 | Olson et al. | |
| 8,062,331 B2 | 11/2011 | Zamierowski | |
| 8,067,662 B2 | 11/2011 | Aali et al. | |
| 8,070,773 B2 | 12/2011 | Zamierowski | |
| 8,114,126 B2 | 2/2012 | Heaton et al. | |
| 8,123,781 B2 | 2/2012 | Zamierowski | |
| 8,142,419 B2 | 3/2012 | Heaton et al. | |
| 8,172,816 B2 | 5/2012 | Kazala et al. | |
| 8,187,237 B2 | 5/2012 | Seegert | |
| 8,188,331 B2 | 5/2012 | Barta et al. | |
| 8,197,467 B2 | 6/2012 | Heaton et al. | |
| 8,207,392 B2 | 6/2012 | Haggstrom et al. | |
| 8,235,955 B2 | 8/2012 | Blott et al. | |
| 8,246,590 B2 | 8/2012 | Hu et al. | |
| 8,246,606 B2 | 8/2012 | Stevenson et al. | |
| 8,257,328 B2 | 9/2012 | Augustine et al. | |
| 8,273,105 B2 | 9/2012 | Cohen et al. | |
| 8,328,776 B2 | 12/2012 | Kelch et al. | |
| 8,337,411 B2 | 12/2012 | Nishtala et al. | |
| 8,353,931 B2 | 1/2013 | Stopek et al. | |
| 8,357,131 B2 | 1/2013 | Olson | |
| 8,376,972 B2 | 2/2013 | Fleischmann | |
| 8,430,867 B2 | 4/2013 | Robinson et al. | |
| 8,447,375 B2 | 5/2013 | Shuler | |
| 8,454,990 B2 | 6/2013 | Canada et al. | |
| 8,460,257 B2 | 6/2013 | Locke et al. | |
| 8,481,804 B2 | 7/2013 | Timothy | |
| 8,486,032 B2 | 7/2013 | Seegert et al. | |
| 8,500,776 B2 | 8/2013 | Ebner | |
| 8,608,776 B2 | 12/2013 | Coward et al. | |
| 8,632,523 B2 | 1/2014 | Eriksson et al. | |
| 8,673,992 B2 | 3/2014 | Eckstein et al. | |
| 8,679,080 B2 | 3/2014 | Kazala et al. | |
| 8,679,153 B2 | 3/2014 | Dennis | |
| 8,680,360 B2 | 3/2014 | Greener et al. | |
| 8,708,984 B2 | 4/2014 | Robinson et al. | |
| 8,721,629 B2 | 5/2014 | Hardman et al. | |
| 8,746,662 B2 | 6/2014 | Poppe | |
| 8,764,732 B2 | 7/2014 | Hartwell | |
| 8,784,392 B2 | 7/2014 | Vess et al. | |
| 8,791,315 B2 | 7/2014 | Lattimore et al. | |
| 8,791,316 B2 | 7/2014 | Greener | |
| 8,801,685 B2 | 8/2014 | Armstrong et al. | |
| 8,802,916 B2 | 8/2014 | Griffey et al. | |
| 8,821,535 B2 | 9/2014 | Greener | |
| 8,945,030 B2 | 2/2015 | Weston | |
| 9,044,579 B2 | 6/2015 | Blott et al. | |
| 9,061,095 B2 | 6/2015 | Adie et al. | |
| 9,180,231 B2 | 11/2015 | Greener | |
| 9,408,755 B2 | 8/2016 | Larsson | |
| 9,421,132 B2 | 8/2016 | Dunn | |
| 9,655,807 B2 | 5/2017 | Locke et al. | |
| 9,737,649 B2 | 8/2017 | Begin et al. | |
| D805,039 S | 12/2017 | Dejanovic et al. | |
| 9,849,023 B2 | 12/2017 | Hall et al. | |
| 10,143,485 B2 | 12/2018 | Locke et al. | |
| 2001/0034499 A1 | 10/2001 | Sessions et al. | |
| 2002/0077661 A1 | 6/2002 | Saadat | |
| 2002/0161346 A1 | 10/2002 | Lockwood et al. | |
| 2004/0162512 A1 | 8/2004 | Liedtke et al. | |
| 2004/0267312 A1 | 12/2004 | Kanner et al. | |
| 2005/0107731 A1 | 5/2005 | Sessions | |
| 2005/0142331 A1 | 6/2005 | Anderson et al. | |
| 2005/0209574 A1 | 9/2005 | Boehringer et al. | |
| 2005/0267424 A1 | 12/2005 | Eriksson et al. | |
| 2006/0020269 A1 | 1/2006 | Cheng | |
| 2006/0058842 A1 | 3/2006 | Wilke et al. | |
| 2006/0069357 A1 | 3/2006 | Marasco | |
| 2006/0155260 A1 | 7/2006 | Blott et al. | |
| 2006/0217795 A1 | 9/2006 | Besselink et al. | |
| 2006/0271018 A1 | 11/2006 | Korf | |
| 2007/0052144 A1 | 3/2007 | Knirck et al. | |
| 2007/0104941 A1 | 5/2007 | Kameda et al. | |
| 2007/0118096 A1 | 5/2007 | Smith et al. | |
| 2007/0123973 A1 | 5/2007 | Roth et al. | |

(56) References Cited

U.S. PATENT DOCUMENTS

| | | |
|---|---|---|
| 2007/0129660 A1 | 6/2007 | McLeod et al. |
| 2007/0149910 A1 | 6/2007 | Zocher |
| 2007/0179421 A1 | 8/2007 | Farrow |
| 2007/0185463 A1 | 8/2007 | Mulligan |
| 2007/0213597 A1 | 9/2007 | Wooster |
| 2007/0282309 A1 | 12/2007 | Bengtson et al. |
| 2008/0041401 A1 | 2/2008 | Casola et al. |
| 2008/0108977 A1 | 5/2008 | Heaton et al. |
| 2008/0243096 A1 | 10/2008 | Svedman |
| 2008/0275409 A1 | 11/2008 | Kane et al. |
| 2008/0306456 A1 | 12/2008 | Riesinger |
| 2009/0005716 A1 | 1/2009 | Abuzaina et al. |
| 2009/0099519 A1 | 4/2009 | Kaplan |
| 2009/0105670 A1 | 4/2009 | Bentley et al. |
| 2009/0204423 A1 | 8/2009 | Degheest et al. |
| 2009/0312685 A1 | 12/2009 | Olsen et al. |
| 2010/0022990 A1 | 1/2010 | Karpowicz et al. |
| 2010/0047324 A1 | 2/2010 | Fritz et al. |
| 2010/0081983 A1 | 4/2010 | Zocher et al. |
| 2010/0137775 A1 | 6/2010 | Hu et al. |
| 2010/0150991 A1 | 6/2010 | Bernstein |
| 2010/0160874 A1 | 6/2010 | Robinson et al. |
| 2010/0179515 A1 | 7/2010 | Swain et al. |
| 2010/0198128 A1 | 8/2010 | Turnlund et al. |
| 2010/0262106 A1 | 10/2010 | Hartwell |
| 2010/0280468 A1 | 11/2010 | Haggstrom et al. |
| 2010/0312159 A1 | 12/2010 | Aali et al. |
| 2011/0021965 A1 | 1/2011 | Karp et al. |
| 2011/0022082 A1 | 1/2011 | Burke et al. |
| 2011/0059291 A1 | 3/2011 | Boyce et al. |
| 2011/0066096 A1 | 3/2011 | Svedman |
| 2011/0082480 A1 | 4/2011 | Viola |
| 2011/0110996 A1 | 5/2011 | Schoenberger et al. |
| 2011/0112458 A1 | 5/2011 | Holm et al. |
| 2011/0178451 A1 | 7/2011 | Robinson et al. |
| 2011/0213319 A1 | 9/2011 | Blott et al. |
| 2011/0224631 A1 | 9/2011 | Simmons et al. |
| 2011/0224632 A1 | 9/2011 | Zimnitsky et al. |
| 2011/0224634 A1 | 9/2011 | Locke et al. |
| 2011/0264138 A1 | 10/2011 | Avelar et al. |
| 2011/0270301 A1 | 11/2011 | Cornet et al. |
| 2011/0305736 A1 | 12/2011 | Wieland et al. |
| 2012/0016321 A1 | 1/2012 | Wu et al. |
| 2012/0029455 A1 | 2/2012 | Perez-Foullerat et al. |
| 2012/0059412 A1 | 3/2012 | Fleischmann |
| 2012/0130327 A1 | 5/2012 | Marquez |
| 2012/0136326 A1 | 5/2012 | Croizat et al. |
| 2012/0136328 A1 | 5/2012 | Johannison et al. |
| 2012/0143113 A1 | 6/2012 | Robinson et al. |
| 2012/0172926 A1 | 7/2012 | Hotter |
| 2012/0191132 A1 | 7/2012 | Sargeant |
| 2012/0209226 A1 | 8/2012 | Simmons et al. |
| 2012/0209227 A1 | 8/2012 | Dunn |
| 2012/0238931 A1 | 9/2012 | Rastegar et al. |
| 2012/0253302 A1 | 10/2012 | Corley |
| 2013/0012891 A1 | 1/2013 | Gross et al. |
| 2013/0023842 A1 | 1/2013 | Song |
| 2013/0066365 A1 | 3/2013 | Belson et al. |
| 2013/0110058 A1 | 5/2013 | Adie et al. |
| 2013/0150813 A1 | 6/2013 | Gordon et al. |
| 2013/0190705 A1 | 7/2013 | Vess et al. |
| 2013/0197457 A1 | 8/2013 | Kazala, Jr. et al. |
| 2013/0204213 A1 | 8/2013 | Heagle et al. |
| 2013/0245527 A1 | 9/2013 | Croizat et al. |
| 2013/0325142 A1 | 12/2013 | Hunter et al. |
| 2013/0331757 A1 | 12/2013 | Belson |
| 2014/0094730 A1 | 4/2014 | Greener et al. |
| 2014/0163415 A1 | 6/2014 | Zaiken et al. |
| 2014/0180229 A1 | 6/2014 | Fuller et al. |
| 2014/0195004 A9 | 7/2014 | Engqvist et al. |
| 2014/0249495 A1 | 9/2014 | Mumby et al. |
| 2014/0316359 A1 | 10/2014 | Collinson et al. |
| 2014/0343518 A1 | 11/2014 | Riesinger |
| 2015/0030806 A1 | 1/2015 | Fink |
| 2015/0057762 A1 | 2/2015 | Harms et al. |
| 2015/0065805 A1 | 3/2015 | Edmondson et al. |
| 2015/0065968 A1 | 3/2015 | Sealy et al. |
| 2015/0100008 A1 | 4/2015 | Chatterjee |
| 2015/0119837 A1 | 4/2015 | Thompson, Jr. et al. |
| 2015/0157758 A1 | 6/2015 | Blücher et al. |
| 2015/0190288 A1 | 7/2015 | Dunn et al. |
| 2015/0196431 A1 | 7/2015 | Dunn et al. |
| 2015/0216732 A1 | 8/2015 | Hartwell et al. |
| 2015/0320602 A1 | 11/2015 | Locke et al. |
| 2015/0374561 A1 | 12/2015 | Hubbard, Jr. et al. |
| 2016/0144085 A1 | 5/2016 | Melin et al. |
| 2016/0184496 A1 | 6/2016 | Jaecklein et al. |
| 2017/0065751 A1 | 3/2017 | Toth |
| 2017/0281838 A1 | 10/2017 | Dunn |

FOREIGN PATENT DOCUMENTS

| | | |
|---|---|---|
| CN | 101112326 A | 1/2008 |
| CN | 101744688 A | 6/2010 |
| CN | 201519362 U | 7/2010 |
| CN | 102038575 A | 5/2011 |
| CN | 202568632 U | 12/2012 |
| CN | 103071197 A | 5/2013 |
| CN | 203408163 U | 1/2014 |
| DE | 2949920 A1 | 3/1981 |
| EP | 1320342 A1 | 6/2003 |
| EP | 2279016 A1 | 2/2011 |
| EP | 2567717 A1 | 3/2013 |
| EP | 2601984 A2 | 6/2013 |
| GB | 2389794 A | 12/2003 |
| GB | 2423019 A | 8/2006 |
| GB | 2489947 A | 10/2012 |
| GB | 2496310 A | 5/2013 |
| JP | S62-57560 A | 3/1987 |
| JP | 2006-528038 A | 12/2006 |
| JP | 2009-525087 A | 7/2009 |
| JP | 2012-105840 A | 6/2012 |
| RU | 1818103 A1 | 5/1993 |
| RU | 62504 U1 | 4/2007 |
| WO | WO 01/85248 A1 | 11/2001 |
| WO | WO 01/89392 A2 | 11/2001 |
| WO | WO 02/05737 A1 | 1/2002 |
| WO | WO 03/003948 A1 | 1/2003 |
| WO | WO 03/049598 A2 | 6/2003 |
| WO | WO 2005/046761 A1 | 5/2005 |
| WO | WO 2005/105174 A1 | 11/2005 |
| WO | WO 2006/046060 A2 | 5/2006 |
| WO | WO 2008/027449 A2 | 3/2008 |
| WO | WO 2008/064502 A1 | 6/2008 |
| WO | WO 2008/104609 A1 | 9/2008 |
| WO | WO 2009/112062 A1 | 9/2009 |
| WO | WO 2010/033725 A2 | 3/2010 |
| WO | WO 2010/097570 A1 | 9/2010 |
| WO | WO 2011/023384 A1 | 3/2011 |
| WO | WO 2011/116691 A1 | 9/2011 |
| WO | WO 2012/082716 A2 | 6/2012 |
| WO | WO 2012/082876 A1 | 6/2012 |
| WO | WO 2012/136707 A1 | 10/2012 |
| WO | WO 2012/142473 A1 | 10/2012 |
| WO | WO 2013/012381 A1 | 1/2013 |
| WO | WO 2013/043258 A1 | 3/2013 |
| WO | WO 2013/071243 A2 | 5/2013 |
| WO | WO 2013/076450 A1 | 5/2013 |
| WO | WO 2014/178945 * | 5/2013 |
| WO | WO 2013/079947 A1 | 6/2013 |
| WO | WO 2013/175309 A1 | 11/2013 |
| WO | WO 2013/175310 A2 | 11/2013 |
| WO | WO 2014/013348 A2 | 1/2014 |
| WO | WO 2014/140578 A1 | 9/2014 |
| WO | WO 2014/158526 A1 | 10/2014 |
| WO | WO 2014/165275 A1 | 10/2014 |
| WO | WO 2014/178945 A1 | 11/2014 |
| WO | WO 2014/194786 A1 | 12/2014 |
| WO | WO 2015/008054 A1 | 1/2015 |
| WO | WO 2015/061352 A2 | 4/2015 |
| WO | WO 2016/179245 * | 5/2015 |
| WO | WO 2015/109359 A1 | 7/2015 |
| WO | WO 2015/110409 A1 | 7/2015 |
| WO | WO 2015/110410 A1 | 7/2015 |

(56) References Cited

FOREIGN PATENT DOCUMENTS

| WO | WO 2015/169637 A1 | 11/2015 |
| WO | WO 2015/193257 A1 | 12/2015 |
| WO | WO 2016/018448 A1 | 2/2016 |
| WO | WO 2016/176513 A1 | 11/2016 |
| WO | WO 2016/179245 A1 | 11/2016 |
| WO | WO 2017/106576 A1 | 6/2017 |
| WO | WO 2018/038665 A1 | 3/2018 |
| WO | WO 2018/041805 A1 | 3/2018 |
| WO | WO 2018/044944 A1 | 3/2018 |
| WO | WO 2018/044949 A1 | 3/2018 |
| WO | WO 2018/085457 A1 | 5/2018 |
| WO | WO 2018/140386 A2 | 8/2018 |

OTHER PUBLICATIONS

International Search Report and Written Opinion for Application No. PCT/EP2018/072296, dated Nov. 8, 2018, 16 pages.

"Definition of 3D Printer," American Heritage Dictionary of the English Language, Fifth Edition, accessed on Feb. 22, 2018 from URL:https://www.thefreedictionary.com, 2016, 1 page.

"Definition of Adhere," The Free Dictionary, accessed on Mar. 23, 2017 from http://www.thefreedictionary.com/adhere, 6 pages.

"Definition of Oculiform," Webster's Revised Unabridged Dictionary, accessed from The Free Dictionary on May 30, 2018 from URL: https://www.thefreedictionary.com/Oculiform, 1913, 1 page.

"Definition of Throughout," Merriam-Webster Dictionary, accessed on Aug. 29, 2017 from https://www.merriam-webster.com/dictionary/throughout, 11 pages.

Hougaard, et al., "The Open Abdomen: Temporary Closure with a Modified Negative Pressure Therapy Technique," International Wound Journal, ISSN 1742-4801, 2014, pp. 13-16.

Kapischke M., et al., "Self-Fixating Mesh for the Lichtenstein Procedure—a Prestudy," Langenbecks Arch Surg, 2010, vol. 395, pp. 317-322.

International Preliminary Report on Patentability for Application No. PCT/EP2018/072296, dated Mar. 12, 2020, 10 pages.

* cited by examiner

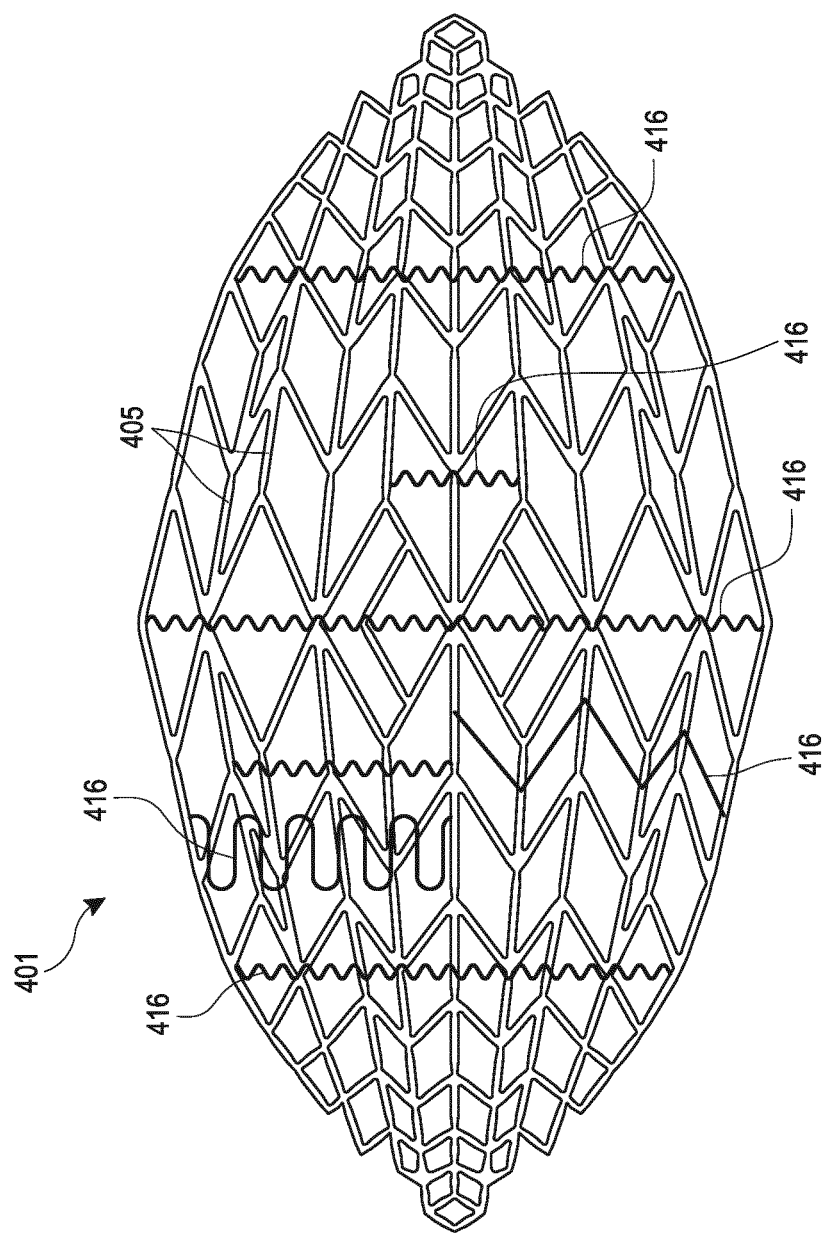

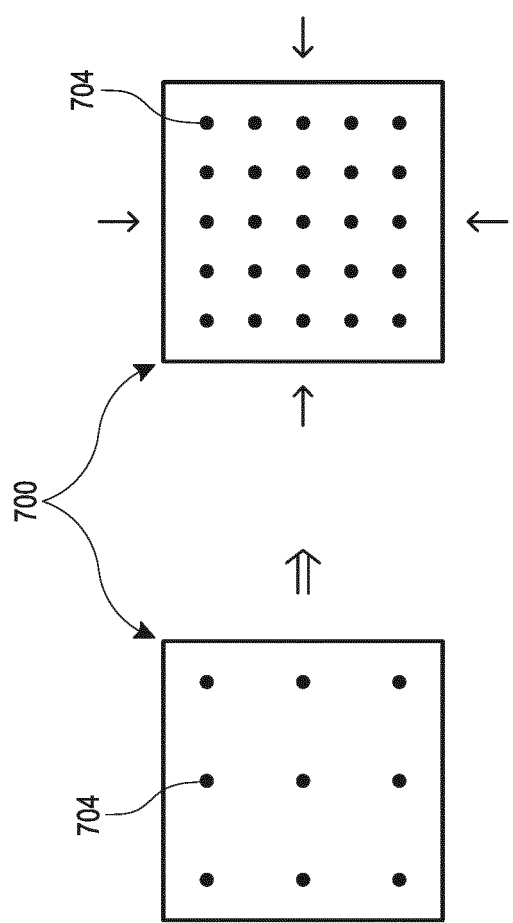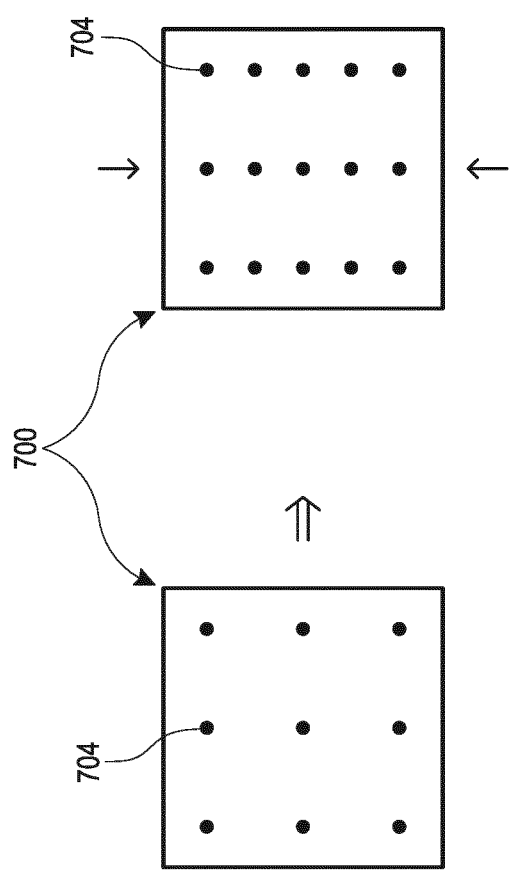

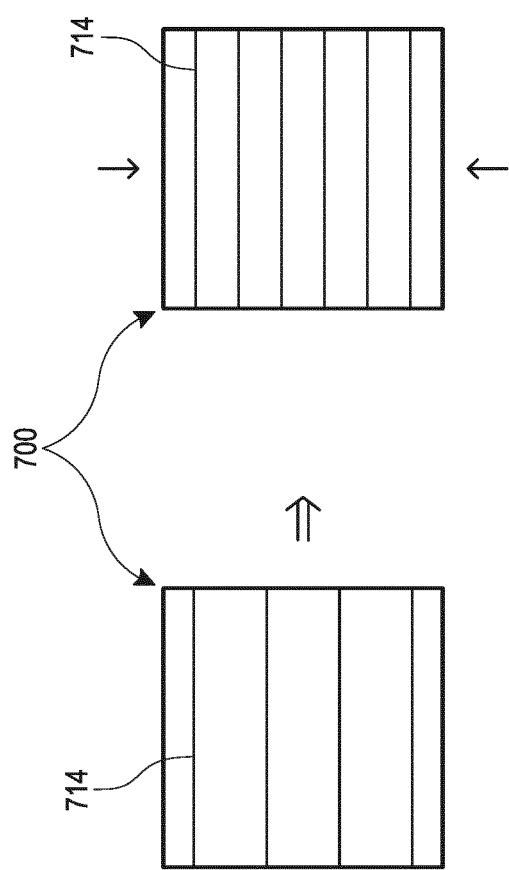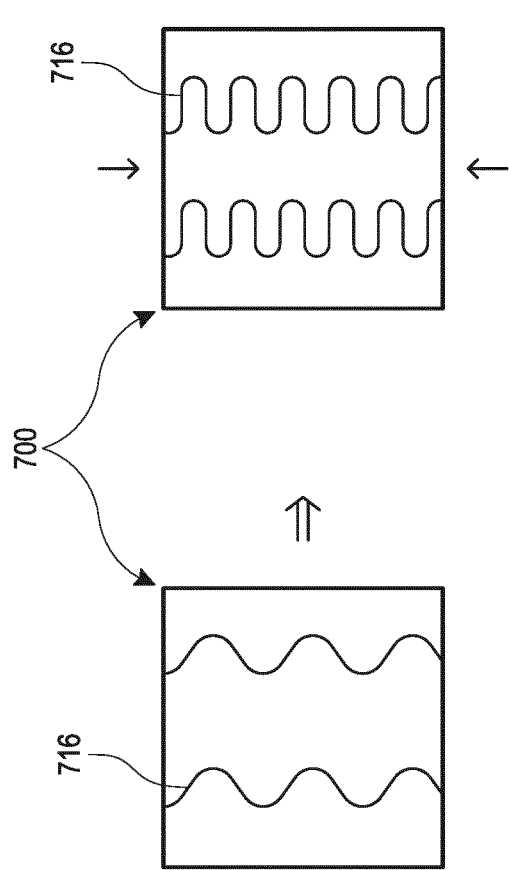

SYSTEMS AND METHODS FOR MONITORING WOUND CLOSURE

CROSS-REFERENCE TO RELATED APPLICATIONS

This application is a U.S. national stage application of International Patent Application No. PCT/EP2018/072296, filed Aug. 17, 2018, which claims the benefit of U.S. Application No. 62/551,646, filed Aug. 29, 2017, the disclosure of each of which is hereby incorporated by reference in its entirety.

BACKGROUND

Field

This application describes embodiments of apparatuses, methods, and systems for the treatment of wounds, specifically for the measurement of the amount of wound closure.

Description of the Related Art

Negative pressure wound therapy has been used in the treatment of wounds, and in many cases can improve the rate of healing while also removing exudates and other deleterious substances from the wound site.

Abdominal compartment syndrome is caused by fluid accumulation in the peritoneal space due to edema and other such causes, and results in greatly increased intra-abdominal pressure that may cause organ failure eventually resulting in death. Causes may include sepsis or severe trauma. Treatment of abdominal compartment syndrome may require an abdominal incision to permit decompression of the abdominal space, and as such, a large wound may be created onto the patient. Closure of this wound, while minimizing the risk of secondary infections and other complications, and after the underlying edema has subsided, then becomes a priority. However, acute open abdominal conditions may be caused by other reasons in addition to compartment syndrome, as described further below.

Other large or incisional wounds, either as a result of surgery, trauma, or other conditions, may also require closure. For example, wounds resulting from sterniotomies, fasciotomies, and other abdominal wounds may require closure. Wound dehiscence of existing wounds is another complication that may arise, possibly due to incomplete underlying fascial closure, or secondary factors such as infection.

Existing negative pressure treatment systems, while permitting eventual wound closure, still require lengthy closure times. Although these may be combined with other tissue securement means, such as sutures, there is also a risk that underlying muscular and fascial tissue is not appropriately reapproximated so as to permit complete wound closure. Further, when foam or other wound fillers are inserted into the wound, the application of negative pressure to the wound and the foam may cause atmospheric pressure to bear down onto the wound, compressing the foam downward and outward against the margins of the wound. This downward compression of the wound filler slows the healing process and slows or prevents the joining of wound margins. Additionally, inflammation of the fascia in the form of certain types of fasciitis can lead to rapid and excessive tissue loss, potentially meriting the need for more advanced negative pressure treatment systems. Accordingly, there is a need to provide for an improved apparatus, method, and system for the treatment and closure of wounds.

SUMMARY

Disclosed embodiments relate to systems, devices, and methods for assessing dimensional changes in medical devices implanted into or attached to a human or animal body. The medical device can be a wound filler and the assessment of dimensional changes may provide a measurement of the degree of wound closure as the wound filler is compressed by the closing wound.

In some embodiments, a wound therapy system comprises a wound filler configured to be at least partially inserted into a wound; a conductive element coupled to the wound filler, wherein a density of the conductive element increases within a detection area of the wound filler upon compression of the wound filler; and a detection device configured to assess a degree of wound closure based on a measurement of the density of the conductive element in the detection area, wherein the density is dependent on the amount of compression of the wound filler.

The system of the preceding paragraph can be used with any of the following features. The measurement may comprise a measurement of the dielectric constant of the detection area of the wound filler, wherein the dielectric constant changes based on a compression of the wound filler.

The system of any of preceding paragraphs can be used with any of the following features. The conductive element may be a conductive filler embedded at least in the detection area of the wound filler.

The system of any of preceding paragraphs can be used with any of the following features. The conductive element may be a plurality of conductive elements spaced across at least the detection area of the wound filler.

The system of any of preceding paragraphs can be used with any of the following features. The wound filler may be configured to be compressed in a first direction and not substantially compressed in a second direction, the second direction being perpendicular to the first direction. The conductive element can be a plurality of conductive wires, each conductive wire comprising a length extending from a first end to a second end. The conductive wires can be arranged substantially parallel to one another and so that the lengths of the conductive wires extend along the second direction.

The system of any of preceding paragraphs can be used with any of the following features. The conductive element may be substantially flexible.

The system of any of preceding paragraphs can be used with any of the following features. The substantially flexible conductive element can be a conductive strip having a width defining a lateral dimension and a length defining a longitudinal dimension. The conductive strip may comprise a conductive wire including a plurality of bends spaced across the length of the conductive strip. At least some of the bends can be configured to allow the conductive strip to be compressed or extended along the longitudinal direction such that the density of the conductive wire is increased or decreased along at least a portion of the longitudinal dimension.

The system of any of preceding paragraphs can be used with any of the following features. The measurement may comprise a measurement of the resonant frequency of the flexible conductive element.

The system of any of preceding paragraphs can be used with any of the following features. The bends may form a sinusoidal, serpentine, and/or triangular pattern.

The system of any of preceding paragraphs can be used with any of the following features. One or more fixed density conductive elements can be coupled to the wound filler, wherein the density of the one or more fixed density conductive element does not substantially change upon compression of the wound filler.

The system of any of preceding paragraphs can be used with any of the following features. The detection device can be configured to be calibrated based on the measurement of a detection area including the fixed density conductive element.

The system of any of preceding paragraphs can be used with any of the following features. The system can include a negative pressure source configured to provide negative pressure to a wound. The negative pressure source may be configured to be in fluid communication with the wound filler.

In some embodiments, a method for assessing a degree of wound closure of a wound comprises placing a detection device in proximity of a detection area of a wound filler. The wound filler may include a conductive element coupled to the wound filler, wherein a density of the conductive element increases within the detection area of the wound filler upon compression of the wound filler. The method further comprises using the detection device to make a measurement based on the density of the conductive element in the detection area, wherein the density is dependent on the amount of compression of the wound filler.

The method of any of preceding paragraphs can be used with any of the following features. The method can further comprise calibrating the detection device by using the detection device to take a calibration measurement over an area of the wound filler comprising a fixed density conductive element. A density of the fixed density conductive element does not change upon compression of the wound filler.

The method of any of preceding paragraphs can be used with any of the following features. The method may further comprise relating the measurement to a degree or amount of wound closure.

In some embodiments, a method for assessing a degree of wound closure of a wound by a detection device comprises making a measurement within a detection area of a wound filler at least partially inserted into the wound. The wound filler includes a conductive element coupled to the wound filler, wherein a density of the conductive element increases within the detection area of the wound filler upon compression of the wound filler comprising the detection area. The method further comprises, based on the measurement, indicating a degree of compression of the wound filler.

The method of the preceding paragraph can be used with any of the following features. Making the measurement may comprise applying a voltage to one or more capacitive plates within the detection device, wherein the amount of charge stored on the one or more capacitive plates is configured to be modulated by a dielectric constant of the detection area and wherein the measurement is reflective of the amount of charge stored on the one or more capacitive plates.

The method of any of preceding paragraphs can be used with any of the following features. The conductive element may be a flexible conductive strip having a width defining a lateral dimension and a length defining a longitudinal dimension. The flexible conductive strip may comprise a conductive wire comprising a plurality of bends spaced across the length of the flexible conductive strip. At least some of the bends may be configured to allow the flexible conductive strip to be compressed or extended along the longitudinal direction such that the density of the conductive wire is increased or decreased along at least a portion of the length of the flexible conductive strip. Making the measurement may comprise transmitting a radio wave toward the flexible conductive strip, receiving a radio wave transmitted from the direction of the flexible conductive strip, and measuring the resonant frequency of the flexible conductive strip. The resonant frequency may be dependent upon the degree of compression experienced by the flexible conductive strip.

In some embodiments, a system for assessing a degree of wound closure of a wound comprising a wound filler and a conductive element according to one or more of the features described in the following description is disclosed.

In some embodiments, a method for assessing a degree of wound closure of a wound comprising a wound filler and a conductive element according to one or more of the features described in the following description is disclosed.

Certain embodiments disclosed herein may provide for quick, convenient, and accurate assessment of conformational changes in a medical device and/or of the degree of wound closure. The embodiments described herein may be used without requiring visual assessment of the wound, wound filler, or other medical device and thus may be especially useful in which visual inspection of the medical device or wound is obstructed or impeded, such as by the application of dressings. The embodiments may allow accurate measurement of wound closure at various locations in the wound. Measurements of wound closure may be correlated to physical dimensions and/or relative amounts and may provide useful information to the clinician, such as when to swap out a wound filler device. Measurements may advantageously be made without removing dressing or bandages from a wound and without placing a detection device in direct contact with the body.

Further features and advantages of at least some of the embodiments of the present disclosure, as well as the structure and operation of various embodiments of the present disclosure, are described in detail below with reference to the accompanying drawings.

BRIEF DESCRIPTION OF THE DRAWINGS

FIGS. 4A-4K schematically illustrate various examples of conductive elements for assessing dimensional changes in a medical device according to some embodiments.

FIG. 5A schematically illustrates the positioning of discrete fixed density conductive elements on a wound-filling matrix. FIG. 5B schematically illustrates the compression of a conductive strip comprising flexible portions and non-flexible portions.

FIGS. 7A-7D schematically illustrate changes in density of conductive elements positioned within a detection area of the detection device according to some embodiments.

DETAILED DESCRIPTION

Figure 1:
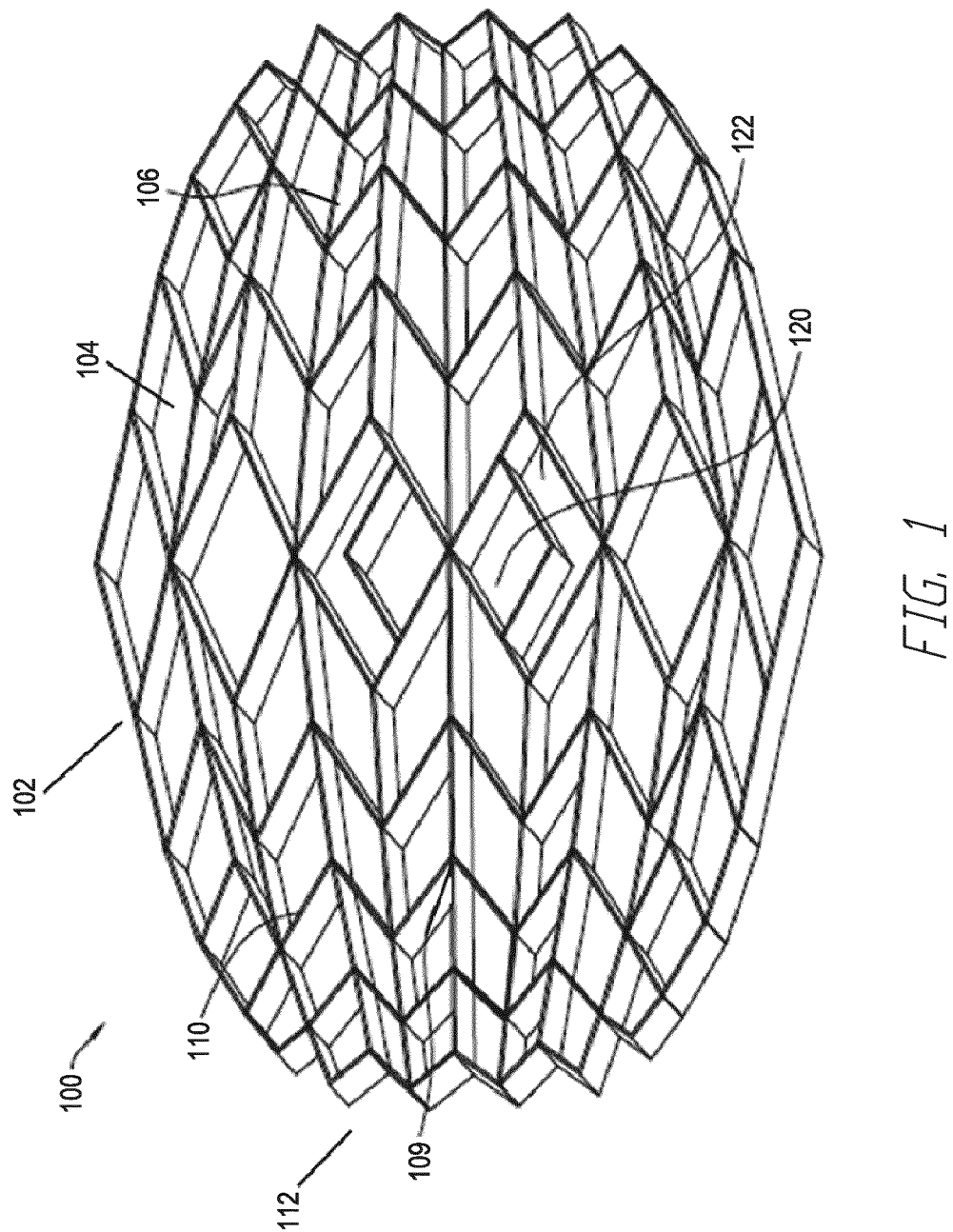
FIG. 1 illustrates an example of a wound-filling matrix according to some embodiments.

In some embodiments, systems disclosed herein can comprise a medical device configured for implantation into a human or animal body and/or for attachment to a human or animal body and a detection device for monitoring the configuration, arrangement, and/or positioning of the medical device. The medical device may be a wound filler, such as a wound-filling matrix, or other type of wound dressing. In some implementations, the detection device may be used to monitor the rate of wound closure and/or to determine a metric of wound closure by analyzing the configuration of the wound filler at a single point in time and/or by comparing readings from multiple time points across a period of time. The medical device may be made of a conductive material or made with a conductive filler, may comprise a flexible conductive element, and/or may comprise an arrangement of discrete conductive elements positioned throughout the medical device, herein referred to collectively as conductive elements. The medical device can be configured such that the configuration, arrangement, and/or positioning of the medical device may modulate the density of the conductive elements, such as the local surface density, at one or more areas across a surface area of the medical device. In some embodiments, the detection device can be configured to assess the configuration, arrangement, and/or positioning of the medical device in or on the body by measuring the dielectric constant (relative permittivity) at the one or more areas of the medical device where the density of conductive elements is able to be modulated. In some embodiments, the dielectric constant may by measured by measuring the change in capacitance of a capacitive plate of the detection device. In some embodiments, the detection device can be configured to assess the configuration, arrangement, and/or positioning of the medical device in or on the body by measuring the resonant frequency of a flexible conductive element.

As used in this section or elsewhere in this specification, the term "horizontal," when referring to a wound, indicates a direction or plane generally parallel to the skin surrounding the wound. The term "vertical," when referring to a wound, generally refers to a direction extending perpendicular to the horizontal plane. The term "longitudinal," when referring to a wound, generally refers to a direction in the horizontal plane taken in a direction along which the wound is longest. The term "lateral," when referring to a wound, generally refers to a direction in the horizontal plane perpendicular to the longitudinal direction. The terms "horizontal," "vertical," "longitudinal," and "lateral" may also be used to describe the stabilizing structures and wound closure devices described throughout this specification. When describing these structures or devices, these terms should not be construed to require that the structures or devices necessarily be placed into a wound in a certain orientation, though in certain embodiments, it may be preferable to do so.

Medical Devices Experiencing Measurable Dimensional Changes

In some embodiments, the medical device may be a wound filler. The wound filler may be a compressible/compactable device or material configured for insertion into a wound (for example, between the open edges of the wound). The wound filler may be configured to stabilize the wound during wound closure/healing (and may be referred to as a stabilizing structure) and may promote or enhance wound healing (for example, by modulating the rate of wound closure). In some embodiments, the wound filler may be a compressible matrix. The matrix may comprise flexible and/or articulable joints or hinges which allow the reorientation of the matrix to progressively accommodate the decreasing area of the wound as the wound closes. The wound filler may be configured for use with negative pressure to promote wound closure.

FIG. 1 illustrates an example of a wound-filling matrix 100 comprising a plurality of elongate strips 106 arranged in parallel or semi-parallel, whose longitudinal length can be aligned with the longitudinal axis of a wound. In embodiments, the elongate strips 106 may also be arranged in a non-parallel fashion. The various cells 104 within this wound-filling matrix 100 may have a variety of shapes and sizes. The length and shape of the elongate strips 106, intervening members 110, and cells 104 may be designed so as to facilitate greater closure of the wound-filling matrix 100. In certain embodiments, the junctions 109 between the elongate strips 106 and intervening members 110 may be thinned to better facilitate rotation and closure of the wound-filling matrix 100. In some embodiments, the wound-filling matrix 100 is tearable and/or frangible, such that the structure may be shaped into the shape of a wound. Tears may be completed at the intersections between intervening members 110 and elongate strips 106 or at any suitable location along the elongate strip 106 or intervening member 110. All wound-filling matrices 100 described herein may be fashioned to accommodate any size of wound.

In certain embodiments, the wound-filling matrix 100 can collapse in any manner described in this section or elsewhere in this specification with or without the application of negative pressure. For example, the wound-filling matrix 100 may collapse significantly more in one plane than in another plane upon application of negative pressure. In some embodiments, the wound-filling matrix 100 is configured to collapse more in a horizontal plane parallel to the length and width of the stabilizing structure than in a vertical plane perpendicular to the horizontal plane. In embodiments, particular rows may collapse in a first direction, while another row may collapse in the same or an opposing direction. In certain embodiments, the wound-filling matrix 100 may collapse along the width of the matrix while remaining relatively rigid along the length of the matrix and in the vertical direction.

The wound-filling matrix 100 may be comprised of any materials described in this section or elsewhere in this specification, including: flexible plastics such as silicone, polyurethane, rigid plastics such as polyvinyl chloride, semi-rigid plastics, semi-flexible plastics, biocompatible materials, composite materials, metals, and foam. In certain embodiments, the stabilizing structure may comprise a radio opaque material, to more readily allow a clinician to find pieces of the stabilizing structure within the wound.

Returning to FIG. 1, wound-filling matrix 100 may have an outer perimeter that defines an at least partially elliptical shape. As described above, wound-filling matrix 100 may comprise a plurality of cells 104 provided side-by-side, each cell 104 defined by one or more walls, each cell 104 having a top end and a bottom end with an opening extending through the top and bottom ends. As with the other stabilizing structures described herein this section and elsewhere in the specification, the wound-filling matrix 100 can be configured to collapse by collapsing one or more cells 104. In some embodiments, the cells 104 are all of the same approximate shape and size; however, in certain embodiments, the cells 104 are of different shapes and sizes. In some embodiments, the wound-filling matrix 100 as described herein this section or elsewhere in the specification may be domed, such that the central portion of the wound-filling matrix 100 structure bulges upward. For example, a lower portion of the wound-filling matrix 100 may be concave, while an upper portion of the wound-filling matrix 100 is convex.

The elongate strips 106 may be made from one single material, such as those described elsewhere in the specification, or the elongate strips may be made from multiple materials. For example, elongate strips 106 may comprise sections of more rigid material and sections of more flexible material. The elongate strips 106 may be curved along their length so as to facilitate the curved outer perimeter of the wound-filling matrix 100. The elongate strips 106 may be curved along their lengths outward away from a center of the wound-filling matrix 100. The arch of the curves of the elongate strips 106 may vary considerably, with some strips 106 being highly curved while other are minimally curved or even straight.

Similarly, the wound-filling matrix 100 can further comprise a plurality of intervening members 110 connected to the elongate strips 106. The intervening members 110 may all be of a similar shape and size or they may be of a variety of shapes and sizes. The intervening members 110 may be constructed from any material disclosed herein this section or elsewhere in the specification. Further, the intervening members 110 may be constructed from multiple materials.

Advantageously, the elliptical shape of the wound-filling matrix 100 may allow the structure to better accommodate the shape of the wound. Most wounds are in shapes that are rounded, thus, an elliptically shaped wound-filling matrix 100 may better fit into a wound.

In embodiments, the outer perimeter 102 may have a reduced edge 112 so as to facilitate collapse of the stabilizing structure. By removing mass of the stabilizing structure at a reduced edge 112, the stabilizing structure can collapse more freely at the reduced edge 112, thus allowing for a better fit within the wound. Further, by reduced the mass at reduced edge 112, there may be less pinching of the surrounding tissue during and after collapse of the stabilizing structure 100.

The wound-filling matrix 100 and all wound fillers and wound closure devices described in this section or elsewhere in this specification can collapse on a variety of timescales in a dynamic fashion. In certain embodiments, the majority of the collapse may occur within the first few minutes upon application of negative pressure. However, after the initial collapse, the wound-filling matrix 100 or wound closure device may continue to collapse at a much slower rate, thereby applying increasing longitudinal tension over a long period of time and drawing the edges of the wound closer together. By slowly drawing the wound edges closer together over time, the wound-filling matrix 100 or wound closure device allows the surrounding healing tissue to remodel synergistically with the closure of the device or wound-filling matrix 100. Slow, dynamic wound closure may allow the surrounding tissue to heal at an accelerated rate, because the collapsing structure or device slowly brings the edges of the wound closer together without stressing the newly formed or weakened tissue too quickly.

In some embodiments, the wound-filling matrices 100 described in this section or elsewhere in this specification can be placed into a wound for a period of time and then removed or replaced with another wound-filling matrix 100. For example, a wound-filling matrix 100 could be inserted into a wound for a period of time, promoting closure of the wound by drawing the edges closer together. After a period of time has passed, the wound-filling matrix 100 can be replaced by a wound-filling matrix 100 of a different size or collapsibility, for example, a wound-filling matrix 100 of a smaller size or decreased density. This process could be repeated over and over, thereby continuously drawing the edges of the wound together over time and allowing for continuing repair and remodeling of the surrounding tissue. In certain embodiments, the wound-filling matrix 100 is configured to remain in the wound for less than about 1 hour, at least about 1 hour, at least about 2 hours, at least about 4 hours, at least about 6 hours, at least about 8 hours, at least about 12 hours, at least about 24 hours, at least about 2 days, at least about 4 days, at least about 6 days, at least about 1 week, at least about 2 weeks, at least about 3 weeks, or more than about 3 weeks.

In certain embodiments, up to 90% of the collapse of the wound-filling matrix 100 or wound closure device may occur within the first few minutes upon application of negative pressure, while the remaining 10% of the collapse may occur slowly over a period of many minutes, hours, days, weeks, or months. In some embodiments, up to about 80% of the collapse, up to about 70%, up to about 60%, up to about 50%, up to about 40%, up to about 30%, up to about 20%, up to about 10%, or about 0% of the collapse will occur immediately within the first few minutes upon application of negative pressure while the remainder of the collapse occurs at a much slower rate such as over the course of many minutes, hours, days weeks, or months. In certain embodiments, the wound-filling matrix 100 can collapse at a variable rate. In some embodiments, the entirety of the collapse occurs at a slowed rate, while in some embodiments the entirety of the collapse occurs almost immediately within the first few minutes. In further embodiments, the collapse can occur at any rate and the rate can vary over time. In certain embodiments, the rate of collapse can be altered in a variable fashion by adding and/or removing portions of the structure or by controlling the application of negative pressure and/or irrigant fluid.

Figure 2:
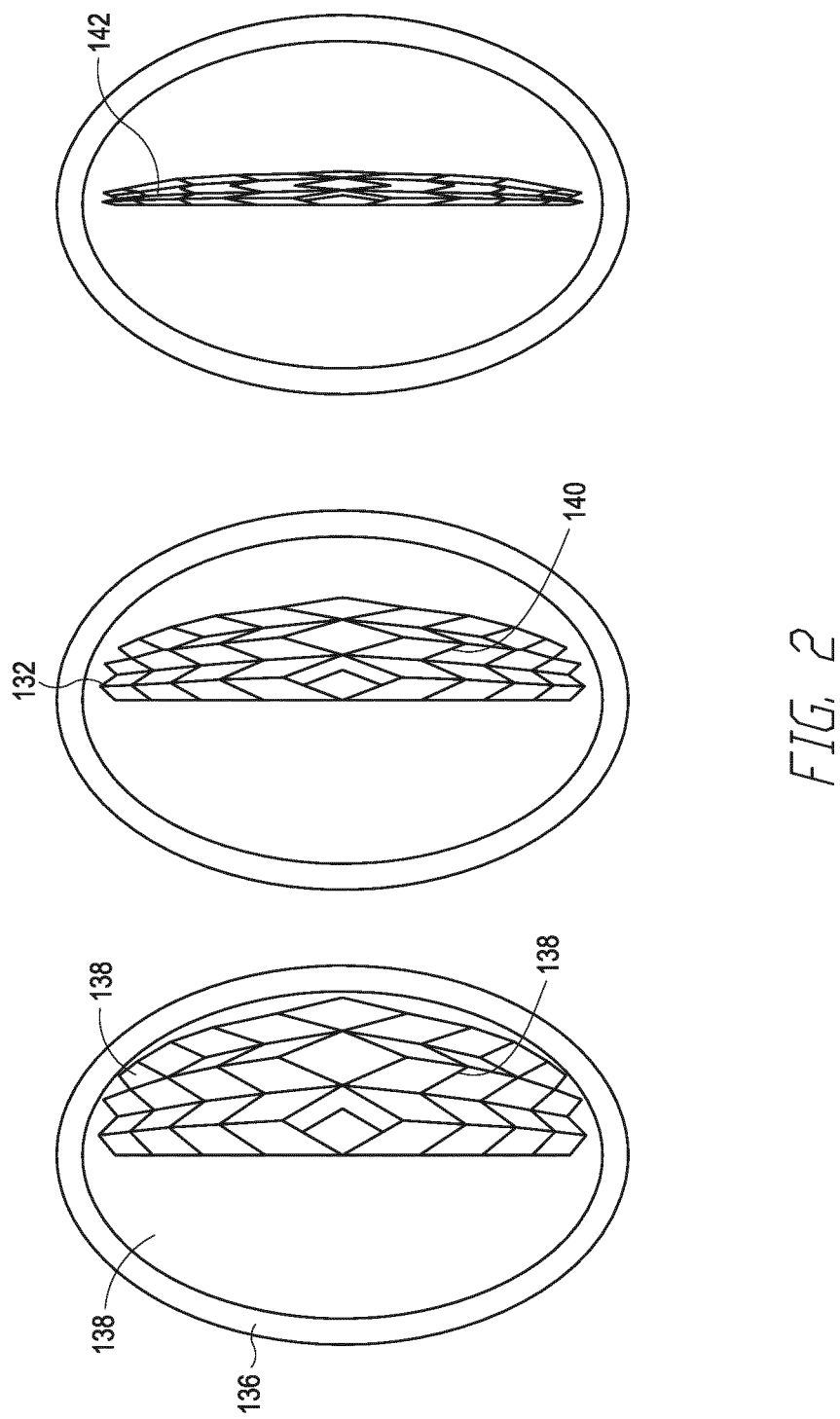
FIG. 2 illustrates the collapse of a wound-filling matrix according to some embodiments.

FIG. 2 illustrates various configurations of collapse of a half-portion of a wound-filling matrix. Each collapsible cell 130 has four sides, and each intersection between an intervening member(s) and/or elongated strip(s) may be modeled via pin-joints 132. Further, the entirety of the wound-filling matrix may be modeled inside of an oval wound model 136. As depicted in FIG. 2, the wound-filling matrix may be modeled to collapse from an open state 138 to a semi-collapsed state 140, to a fully collapsed state 142. In some clinical scenarios, maximum closure down to a completely flattened wound-filling matrix may be desirable to maximize wound closure by drawing the edges of the wound as close together as possible.

The wound-filling matrices 100 and/or wound fillers and/or wound closure devices described in this section or elsewhere in this specification may be used in conjunction with methods or systems for the closure of a wound. In some embodiments of methods of use for closure of a wound, one or more of the wound-filling matrices 100 or wound closure devices of any of the embodiments described in this section or elsewhere in this specification is placed into a wound. In some embodiments, an organ protection layer may be provided in the wound before placement of the wound-filling matrix 100. In certain embodiments, foam or other porous material may be placed in the wound along with the wound-filling matrix 100 or wound closure device, either below, above, or surrounding the wound-filling matrix 100 or wound closure device. Foam or other porous material may also surround the perimeter of the wound-filling matrix 100 or wound closure device. The wound-filling matrix 100 or wound closure device may be configured to collapse in any manner as described in this section or elsewhere in this specification, for example, by having a particular size and shape, or by comprising a certain volume of foam or other porous material within the cells of the structure. The wound-filling matrix 100 or wound closure device may further be altered in any manner described in this section or elsewhere in this specification so as to better accommodate the shape of the wound. After placement in the wound, the wound-filling matrix 100 or wound closure device can be sealed by a fluid-tight drape. The fluid-tight drape can comprise a port configured for the application of negative pressure. A source of negative pressure may then be connected to the port and negative pressure may be applied to the wound. The wound-filling matrix 100 or wound closure device may be replaced over time by wound-filling matrices 100 or wound closure devices of various shapes and sizes as desired to best promote wound healing.

Figure 3:
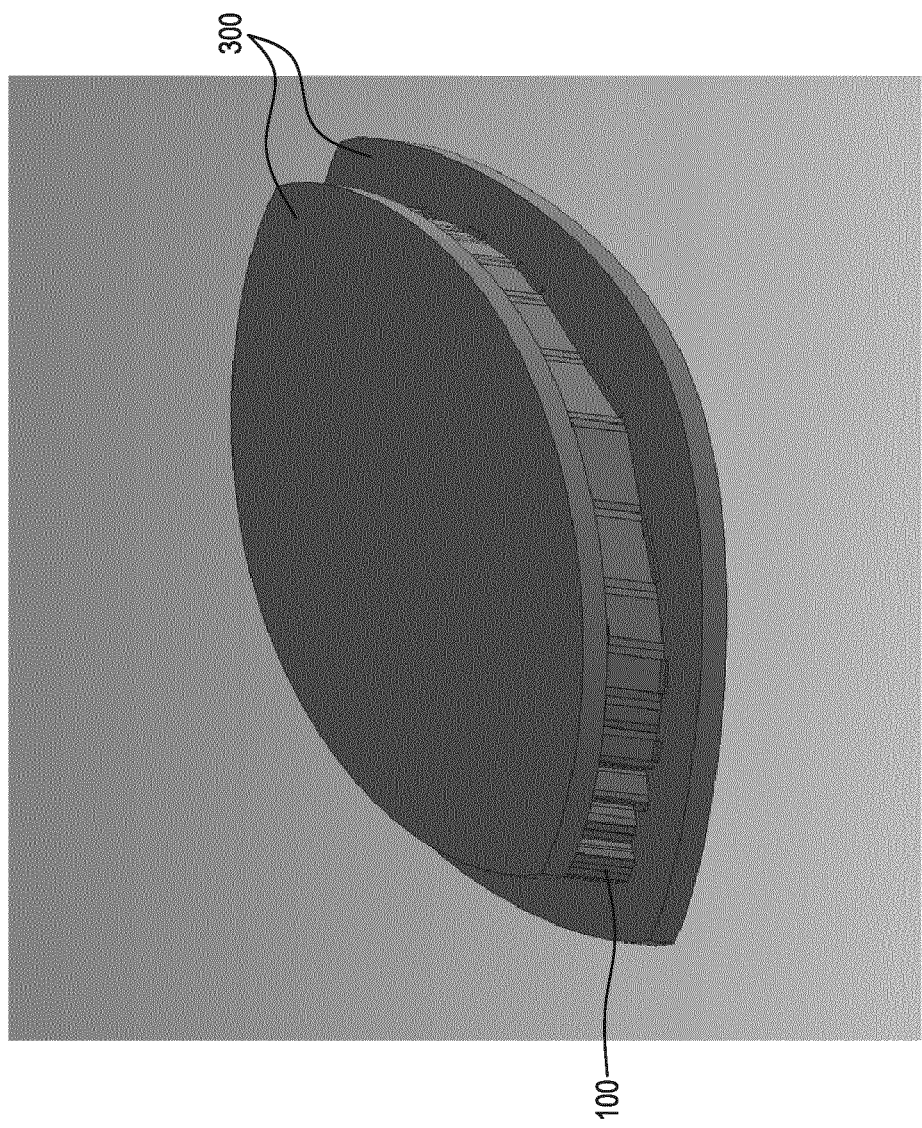
FIG. 3 illustrates a wound filling matrix covered by foam layers according to some embodiments.

FIG. 3 illustrates an example of a wound-filling matrix 100 covered on its top and bottom surfaces by foam layers 300. Foam layers may be positioned on the top and/or bottom surface of wound fillers. The foam layers may help to distribute negative pressure applied from an external negative pressure pump. The foam layers 300 may be placed into the wound, over the wound, under the wound or a combination thereof. The foam layers 300 may be compressible such that they are compressed along with the wound-filling matrix 100 as the wound closes. The foam layers 300 described herein may include any type of foam described herein this section or elsewhere in the specification. Possible foams may include open-celled and/or reticulated foams made from a polymer. Suitable foams include foams composed of, for example, polyurethane, silicone, hydrophobic materials, hydrophilic materials, open-celled materials, close-celled materials, mixed open and close-celled materials, reticulated materials, polyester, silicone, and/or polyvinyl alcohol. In embodiments, the foam layers 300 described herein may include materials that change their properties over time. For example, a particular foam may be rigid initially but become more flexible when wet and/or lose rigidity over time due to degradation of the material. In embodiments of the foam layers, the layers of foam may comprise any type of suitable foam material described herein this section or elsewhere in the specification. For example, the foam may comprise "black foam" such as polyurethane and/or "white foam" comprising polyvinyl alcohol (PVA). In embodiments involving PVA foam, thinner foam layers may be needed as compared to other types of foam, because PVA foam is often more resilient and dense than other types of foam. Further, once PVA foam becomes wet it may also aid with lateral slip. In some embodiments, the foam layers may be combined with other fillers such as gauze, or other mesh/net products such as those on Fry and Kossel. In some embodiments, the foam layer or collective foam layers may be considered the medical device.

In some embodiments, the medical device may be a dressing, drape, wrap, bandage, splint, cast or other support attached to a joint of the body (for example, the elbow, knee, etc.). The support may be at least somewhat flexible. The support may be configured to help stabilize operative equipment attached to the joint. For example, the support may be a dressing surrounding a negative pressure pump operatively connected to an open wound on the joint. The support may be configured to at least partially stabilize the joint. For example, the medical device may be a splint. The medical device may be compressed (for example, squished or forced to fold up on itself) or stretched upon flexion or extension of the joint. In some embodiments, the medical device may be at least somewhat elastic. The systems, devices, and methods disclosed herein may be used to assess the degree of flexion or extension of a joint to which the medical device is attached or in which it is implanted either at a point in time or over a duration of time. For instance, bending of the joint may cause compression or extension of the medical device along the plane of movement. In some implementations, the detection device may be applied to the joint as a sensor. The sensor may be configured to record flexion and/or tension over time and can be used, for example, to assess patient compliance. The sensor may be useful for monitoring either whether the patient is compliant with a healing regimen which requires little or no movement of the joint or whether the patient is compliant with a therapeutic movement or exercise regimen which should involve periodic movement of the joint. In some implementations, the detection device may be a non-contact device (for example, a hand-held instrument). The detection device may be used to measure the angle of a joint. Such a measurement may be especially useful if the precise angle of the joint is difficult to visually perceive and/or measure, such as if the joint is sufficiently concealed and/or covered by the medical device and/or other attachments. Precise angles of the joint may be determinable such as through calibration methods described elsewhere herein.

Incorporation of Conductive Elements for Monitoring Dimensional Changes

In some embodiments, the various medical devices described herein may be defined to have a surface area extending along a horizontal plane. The surface area of the medical device may extend substantially parallel to a surface of the body. The medical device may be positioned on top of a surface of the body, within the surface of the body, underneath the surface of the body, or combinations thereof. The surface area may be relatively flat or may be curved to match the contour of the surface of a body part (for example, an elbow, knee, hip, etc.). The medical devices may be defined to have a thickness extending substantially perpendicular to the surface area of the medical device. The surface area of the medical device may be considered to be on top of the medical device, below the medical device, somewhere between the top surface and the bottom surface, or extending throughout the thickness of the medical device. The systems, devices, and methods disclosed herein may be configured to monitor physical changes in the surface area of the medical device, including, but not limited to, compaction, extension, rearrangement, reconfiguration, and/or bending of the surface area of the medical device. In some embodiments, the systems, device, and methods disclosed herein may alternatively or additionally monitor physical or structural changes in the vertical direction (for example, changes in the density of the thickness of the medical device).

Physical changes in the surface area of the medical device may be obscured from the view of a clinician. For instance, a wound may be covered with foam, gauze, dressing, or other materials which obscure the interior and/or the edges of the wound and/or the wound filler. Therefore, it may be impossible or impracticable for the clinician or other observer to visually detect the changes in the surface area of the medical device and/or corresponding changes in the size of a wound. For instance, a clinician may not be able to discern the amount of wound closure that has occurred over time using a wound filler, without removing layers of material from the wound. Even then, visual assessment of the wound may not provide sufficient quantitative measurement of the changes in wound dimensions. Measurement of the wound using standard measurement tools (for example, rulers, measuring tape, calipers, etc.) may require prolonged exposure of the wound and/or unwanted contacted with the wound.

FIGS. 4A-4K illustrate various examples of conductive elements for use with the medical device as applied to a wound filler medical device 400. In some examples, the wound filler 400 may be a wound-filling matrix 401. In various implementations, the conductive elements may comprise a metal (for example, silver, gold, carbon steel, etc.). The incorporation of the conductive element in or on the medical device may alter (for example, increase) the dielectric constant of the medical device over a localized area where the conductive element is positioned. In some implementations, the dielectric constant may be raised such that the background level, regardless the degree of compression, is elevated above that which would be altered by the presence of wound fluid. In some implementations, the depth of detection may be limited by the detection device to focus on the surface of the medical device, such that, for example, the effect of wound fluid found deeper in the wound is minimized. In some embodiments, the conductive element may be a conductive filler 402 (for example, metal particulate, or powder) which is incorporated directly into the medical device. For instance, the medical device may comprise a polymer (for example, silicone) or foam and the conductive filler 402 may be embedded in the polymer during fabrication. In some implementations, the conductive filler 402 may be uniformly distributed throughout the medical device, as schematically illustrated in the wound filler 400 of FIG. 4A, such that the solid polymer portions of the medical device comprise a relatively homogenous dielectric constant. In some implementations, the conductive filler 402 may be localized to certain areas (for example, flexible joints or articulable components of the medical device), as schematically illustrated in the vertices 403 of the wound-filling matrix 401 of FIG. 4B, such that those areas may be used as conductive markers. The detection device may be used to detect the relative changes in density of the conductive material that occur by rearrangement of the physical structure (for example, the polymer matrix) and/or by bringing the conductive markers closer together or further apart.

Figure 4B:
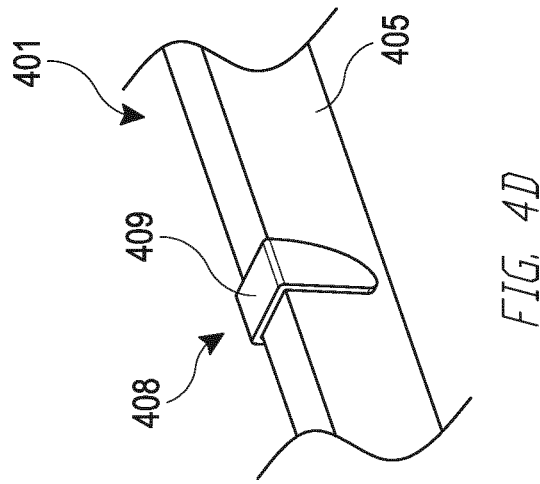
Figure 4D:
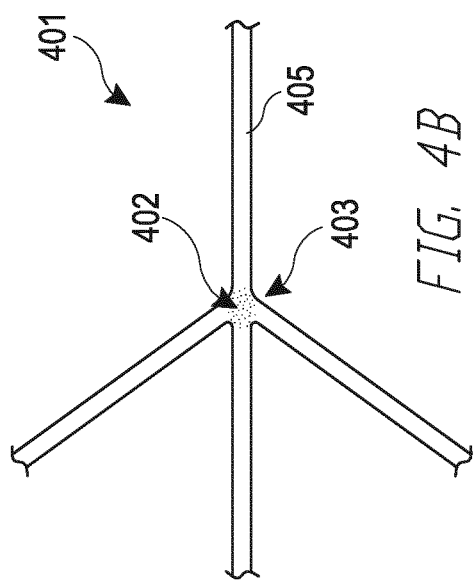
Figure 4A:
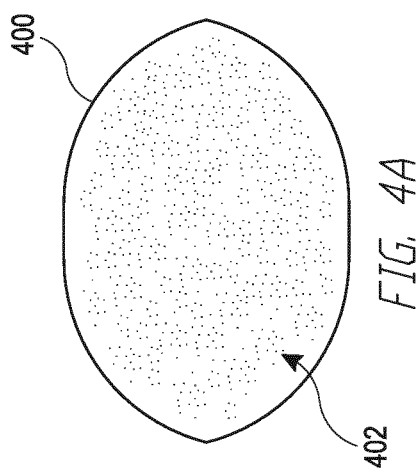
Figure 4C:
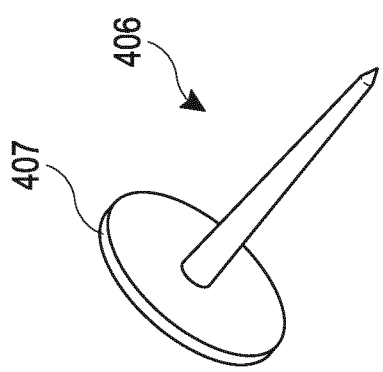
Figure 4E:
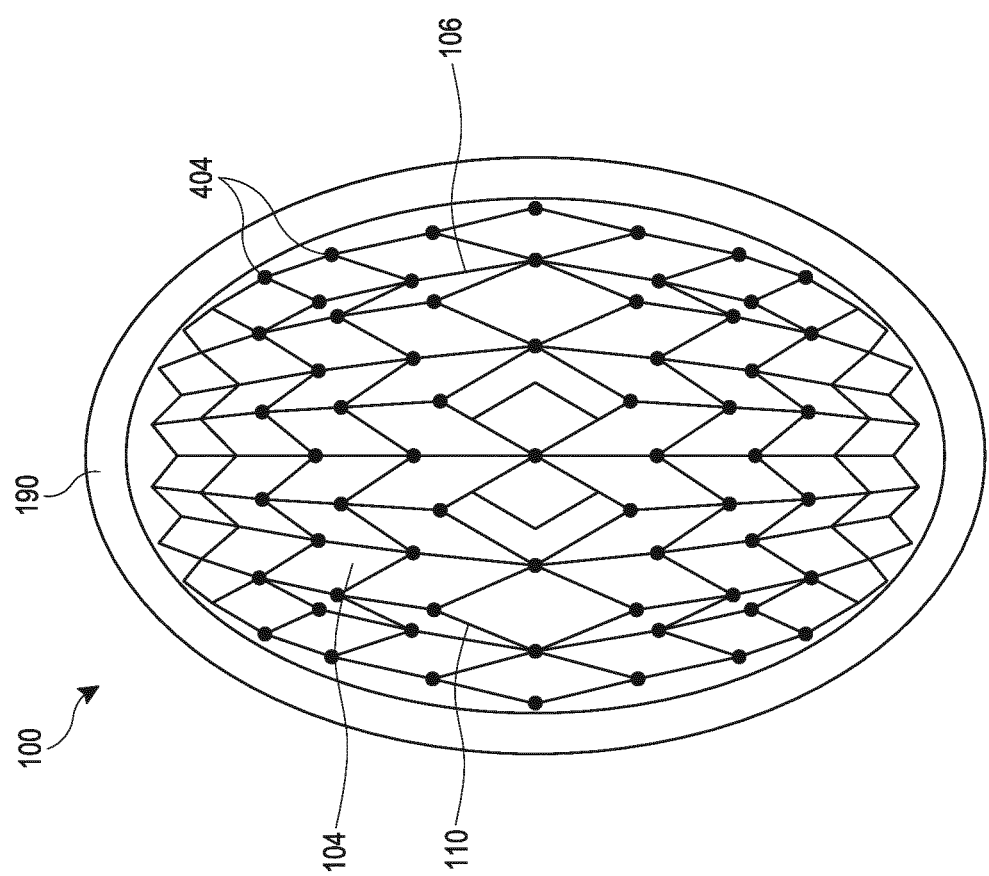

In some embodiments, the conductive elements may be discrete conductive elements 404 positioned strategically throughout the medical device to serve as markers used to track localized density of the medical device. For example, the medical device may comprise conductive inserts or clips. FIG. 4C schematically illustrates an example of an insert 406. The inserts may comprise a long slender body (for example, a cylindrical shaft). The inserts 406 may be configured, for example, as pins or tacks that are inserted into the medical device. FIG. 4D schematically illustrates an example of a clip 408 attached to a wound-filling matrix 401. The clips 408 may be configured, for example, to slide over, clamp to, or otherwise be secured to the elongate strips or intervening members of a wound-filling matrix 401, as described elsewhere herein. The clips 408 may have an elastic bias which secures them to elongate members of the medical device, such as the elongate strips of a wound-filling matrix 401. In some implementations, the length of the discrete conductive element 404 may be used to modulate the relative change in the localized dielectric constant. For instance, longer conductive elements may more measurably alter (for example, increase) the localized dielectric constant of the medical device than shorter conductive elements. Similarly, the surface area of the conductive element 404 may be used to modulate the relative change in the localized dielectric constant. Discrete conductive elements 404 with larger surface areas may more measurably alter the localized dielectric constant of the medical device than discrete conductive elements with smaller surface areas. The discrete conductive elements 404 may be configured with heads, such as heads 407, 409 illustrated in FIGS. 4C and 4D, respectively, that may sit above the top surface of the medical device and act to increase the surface area of the discrete conductive element 404 within a detection area of the detection device. The heads of the discrete conductive elements 404 may be relatively flat to maintain a low profile with the medical device. These discrete conductive elements 404 may be spread across a surface area of the medical device and may extend a depth into the thickness of the medical device. In embodiments comprising a bulk wound filler material, the discrete conductive elements may be distributed substantially uniformly across the surface area of the wound filler or substantially uniformly across localized areas of the wound filler expected to undergo dynamic changes. In embodiments, comprising a wound-filling matrix such as matrix 100, the discrete conductive elements 404 may be positioned at or near one or more of the vertices of the matrix 100, as shown in FIG. 4E. In some embodiments, a discrete conductive element 404 may be positioned at each vertex 109. In some implementations, the discrete conductive elements 404 may be incorporated into the medical device during fabrication of medical device. In some implementations, the discrete conductive elements 404 may be incorporated after the fabrication of the device, either before or after implantation or attachment to the body.

Figure 4H:
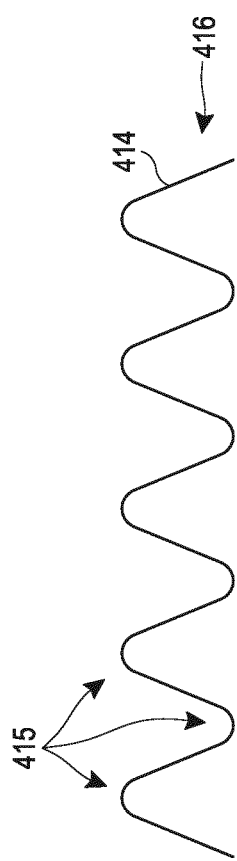
Figure 4I:
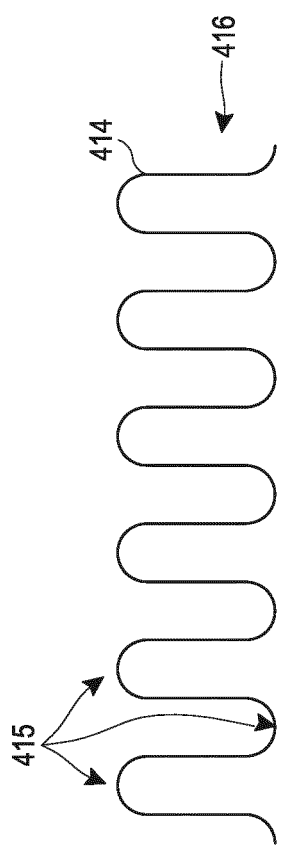
Figure 4J:
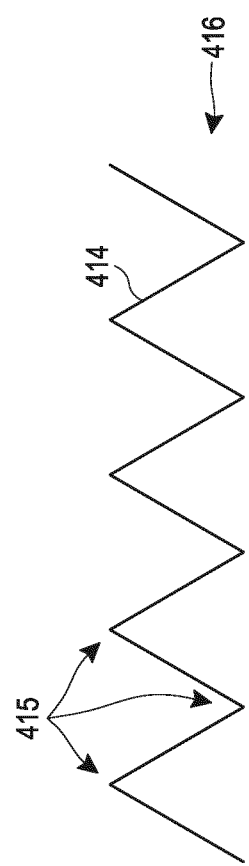
Figure 4F:
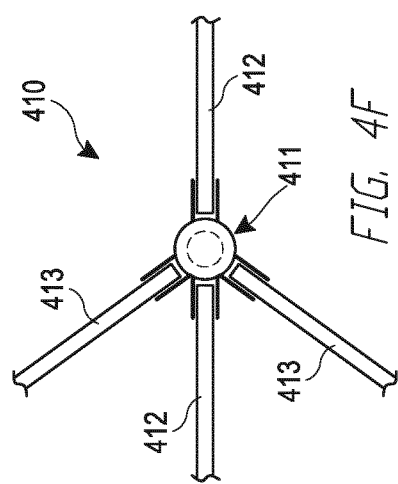

In some embodiments, the medical device may be fabricated with conductive components configured to serve as markers for density changes. For example, as illustrated in FIG. 4F, the medical device may be a wound-filling matrix 410 fabricated with conductive (for example, metal) joints or hinges 411 that join together certain components of the medical device (for example, elongate strips 412 and intervening members 413). These conductive joints 411 may be brought closer together or further apart during use of the medical device, such as when a wound-filling matrix 410 is folded, rotated, or articulated around the joints 411 that form the vertices of the matrix.

Figure 4G:
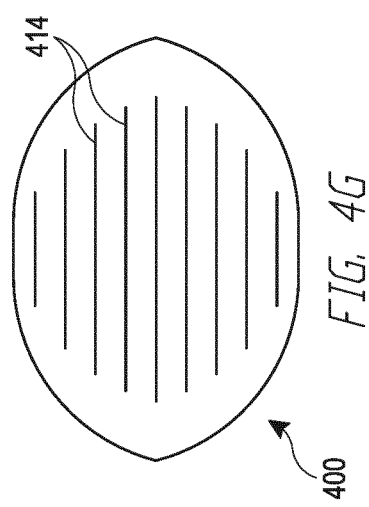

In some embodiments, the conductive element may be one or more conductive wires 414 coupled to the top surface and/or the bottom surface of the medical device or inserted through the medical device parallel to the horizontal plane. FIG. 4G schematically illustrates an example of conductive wires 414 coupled to a wound filler 400. The conductive wires 414 may comprise a length extending from a first end of the conductive wire 414 to a second end of the conductive wire 414. In some embodiments, multiple conductive wires 414 may be positioned relatively parallel or semi-parallel to one another. The conductive wires 414 may be relatively straight. The conductive wires 414 may be curved to conform to the natural contours of the surface of the body. The conductive wires 414 may be spaced across a first direction in which the medical device is expected to experience a measurable change in dimensions (for example, the lateral dimension of a wound filler). The length of the conductive wires 414 may be aligned along a second direction in which the medical device is expected to experience little or no change in dimension (for example, the longitudinal direction of a wound filler). The second direction may be perpendicular to the first direction. The conductive wires 414 may be brought closer together or further apart as the medical device is compacted or extended along the first direction. The conductive wires 414 may be especially suitable for medical devises which experience anisotropic dimensional changes. For instance, the conductive wires 414 may be applied to a wound filler which collapses primarily in one direction to bring opposite edges of the wound closer together. These edges may then be sewed together. In embodiments where the wound filler is an articulable matrix, the conductive wires may be aligned to elongate strips of the matrix. The conductive wires 414 may be coupled by any suitable means. For example, the conductive wires 414 may be glued, stapled, or sewn to the top or bottom surface of the wound filler 400 or embedded directly in the wound filler 400. In embodiments comprising a wound-filling matrix, the conductive wire 414 may be coupled to one or more of the lengths of a longitudinal or transverse member (for example, the elongate strips 106 of wound-filling matrix 100).

In some embodiments, conductive wires 414 may be configured to collapse or expand along a length of the conductive wire 414 upon compressing or extending, respectively, the medical device in that direction. For instance, the conductive wires 414 may comprise bends 415 spaced apart along their length and positioned in a single plane. The bends 415 may be periodic. For example, the bends 415 may shape the conductive wire 414 in a sinusoidal or serpentine pattern having smooth, rounded bends 415, as shown in FIGS. 4H and 4I, respectively, and/or the bends 415 may shape the wire in a zig-zag pattern having sharp, triangular bends, as shown in FIG. 4J. The bends 415 may be configured to expand (an increase in the angle of the bend) upon extension and to collapse (a decrease in the angle of the bend) upon compression. The bends 415 may shape the conductive wire 414 into a flexible conductive element such as a flexible conductive strip 416 comprising a length along a longer dimension (the longitudinal axis of the conductive strip 416) and a width along a shorter dimension (the lateral axis of the conductive strip 416), perpendicular to the longer direction. In some embodiments, the bends 415 may be uniformly spaced such that the conductive strip 416 is a constant width along its length. In some embodiments, the bends 415 may be spaced such that the conductive strip 416 has a varying width along its length.

FIG. 4K schematically illustrates examples of the positioning of various flexible conductive strips 416 on a wound-filling matrix 401. The medical device may incorporate one or more conductive strips 416. In embodiments comprising multiple conductive strips 416, the strips 416 may be the same length or different lengths, the same pattern or different pattern, have the same frequency and/or pitch of bends 425 or different frequencies and/or pitches of bends 425, etc. In embodiments comprising a wound filling matrix, such as matrix 401 shown in FIG. 4K, the conductive strips 416 may be attached, for example, at different points along the longitudinal axis of the matrix 401 to the same elongate strip 405 or to different elongate strips 405. The conductive strip 416 may be configured to impart negligible resistance to compression and/or extension of the medical device along the longitudinal direction of the conductive strip 416. The amount of resistance may increase for larger degrees of compression and/or extension. The resistance of the conductive strip 416 to compression and/or extension may be sufficiently low, even at more extreme degrees of compression and/or extension, such that, for instance, the conductive strip 416 does not impede the reconfiguration of the medical device. For example, the conductive strip 416 may be configured to provide a low enough resistance to compression such that it does not impede or alter the rate of wound closure when coupled to a wound filler. The thickness or gauge of the conductive wire 414 may be relatively thin to facilitate compression and/or extension of the bends 415 along the length of the conductive strip 416. The conductive wire 414 may be fabricated of a material that is relatively flexible (easy to bend) to minimize resistance to compression and/or extension.

The flexible conductive strip 416 may be particularly suitable for assessing anisotropic changes in dimensions of medical devices, particularly changes in a single dimension. The compression or extension of the conductive strip 416 along its longitudinal axis increases or decreases, respectively, the density of the conductive material along the longitudinal direction between the first end and second end of the conductive wire 414. For instance, the compression of a conductive strip 416 may amplify the relative change in the density of conductive material for a given compressive strain relative to bringing together spaced, discrete conductive elements 404. The flexible conductive strip 416 may also provide a relatively uniform measure of density along the length of the conductive strip 416 relative to spaced, discrete conductive elements 404. The spacing of the bends 415 and/or the sharpness of the bends 415 may be used to modulate the relative changes in density upon given amounts of compression and/or extension. The bend spacing and bend angle parameters may be used to optimize the range of relative changes in the density of conductive material. The optimization may depend on the size of the detection area of the detection device, described elsewhere herein. The periodic bends 415 of the conductive strip 416 may bridge gaps in the medical device (for example, gaps in a wound-filling matrix 401) such that density changes can be monitored whether or not the detection area of the detection device is large enough to span the gaps of the medical device. The conductive strips 416 may be strategically coupled to the medical device to target localized areas where dimensional changes are expected to occur. The conductive strips 416 may be strategically positioned such that the longitudinal axis of the conductive strip 416 is aligned with a dimension of the medical device expected to experience dimensional change (for example, anisotropic change). In some embodiments, the conductive strip 416 may be slightly elevated above the top surface of the medical device to avoid interfering with the compression of the device (for example, becoming pinched between collapsing members of a wound-filling matrix).

The flexible conductive strip 416 may be coupled to a non-conductive element. For example, the conductive strip 416 may be joined to a fabric. The fabric may be elastic to allow for the compression or extension of the conductive strip 416. In some implementations, the conductive strip 416 may be sewn or otherwise embedded into a non-conductive fabric strip (for example, between a top layer of fabric and a bottom layer of fabric). The non-conductive fabric strip may be used to readily couple the conductive strip to the surface of the medical device, for instance, by stapling, gluing, pinning, etc. The non-conductive fabric strip may be coupled at two ends of the fabric strip to the medical device or it may be coupled at multiple points along the length of the fabric strip. Coupling the conductive strip 416 to the medical device (for example, via coupling of the non-conductive strip) may effectively divide the conductive strip 416 into portions which may experience different degrees of compression/extension. Measuring the differences in density between the portions may indicate relative degrees of difference in the compression or expansion of the medical device along the longitudinal axis of the conductive strip 416.

Any of the conductive elements disclosed herein, including the flexible conductive strip 416, may be coupled to a wound filler, such as a wound-filling matrix, by embedding the conductive element into the wound-filler or bonding the conductive element to the surface of the wound filler. For instance, the conductive elements may be embedded in or bonded to the elongate strips and/or intervening members of a wound-filling matrix. For example, the conductive elements may be printed, thermally printed, thermally bonded or woven into the wound filler. The conductive elements may be inset-cast into the molding of the wound filler. The conductive elements may be bonded by local thermal or ultrasonic/laser welding of the materials, such as where the wound filler comprises a thermoplastic. In some implementations, the solid portions of the wound filler may be configured with sufficient internal spaces or cavities to allow flexing or bending of conductive elements such as flexible conductive strips. In some implementations, the wound filler may be configured with sufficient elasticity to extend or compress along with a flexible conductive element. In some implementations, flexible conductive elements, such as flexible conductive strips 416, may be coupled to a wound-filling matrix such that the bends are positioned at vertices of the matrix and the zig-zag pattern of a flexible conductive strip 416 follows the zig-zag pattern of the matrix.

Figure 5A:
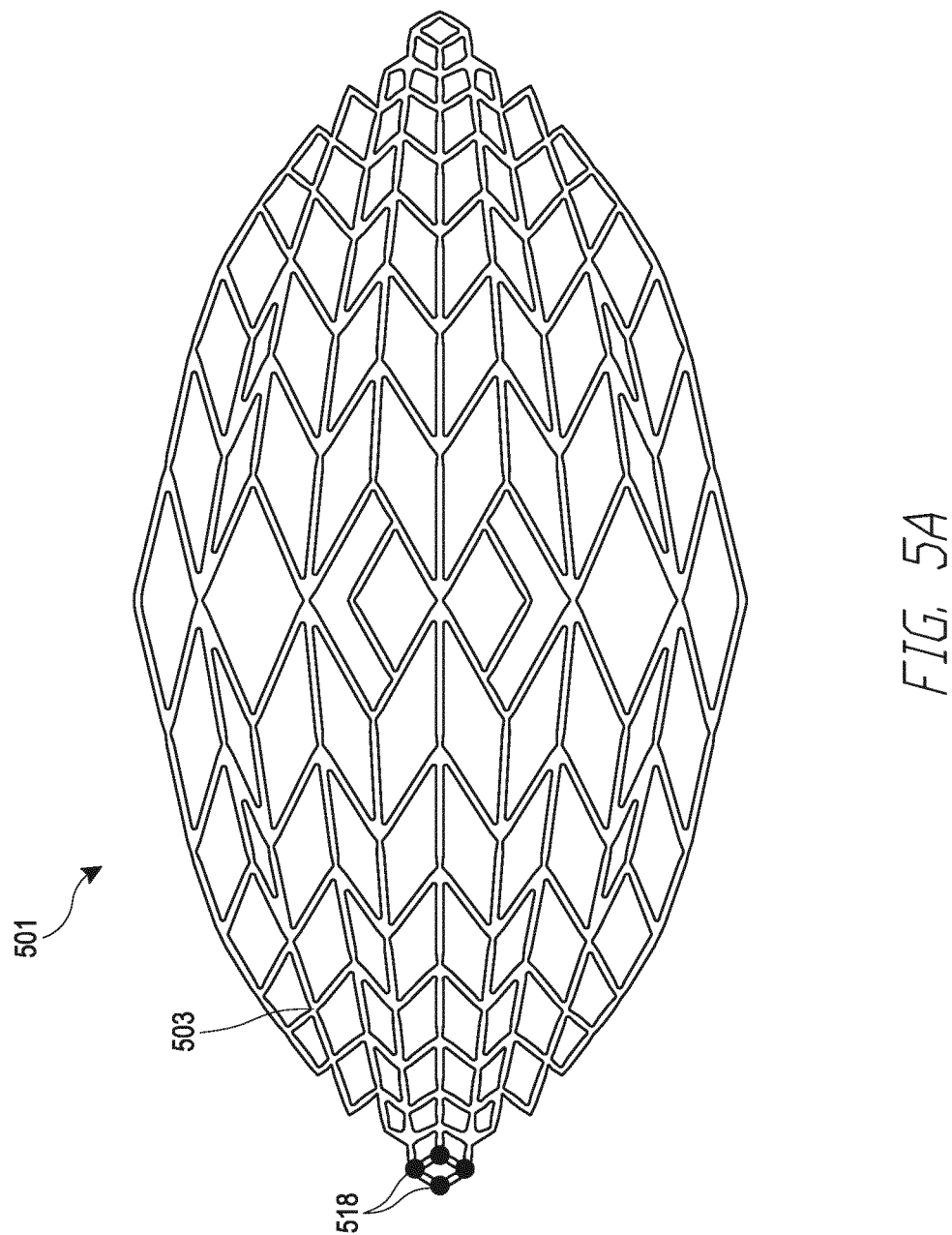
FIGS. 5A-5B schematically illustrate fixed density conductive elements according to some embodiments.

In some implementations, conductive elements of a fixed spatial density may be incorporated into the medical device, referred to herein as fixed density conductive elements 518. The fixed density conductive elements 518 may be used as a reference and/or baseline signal for calibrating the detection device. The fixed density conductive elements 518 can be used to minimized the effects of wound fluid on the detection device. The fixed density conductive elements 518 may be useful in distinguishing detectable changes (for example, changes in dielectric constant) resulting from dimensional changes in the medical device from changes resulting from the presence of wound fluid. The fixed density conductive elements may be useful in assisting a user in holding, placing, or positioning the detection device a suitable distance from the medical device. For example, if the detection device is positioned too far from the fixed density conductive elements 518, the detection device may effectively give a "no signal" reading. The fixed density conductive elements 518 may be the same as the conductive elements described elsewhere herein (for example, discrete conductive elements 404), but may be positioned in an area of the medical device that is known or expected not to undergo any dimensional changes or only to undergo negligible dimensional changes. For example, the fixed density conductive elements 518 may comprise a plurality of discrete conductive elements positioned along vertices of a wound-filling matrix. The fixed density conductive elements 518 may be positioned at portions of a wound filler expected to experience relatively little compaction. For instance, the fixed density conductive elements 518 may be positioned along an edge and/or at a corner of a wound filler. The fixed density conductive elements 518 may be positioned along a midline of the wound filler towards which the device is configured to collapse. FIG. 5A schematically illustrates the positioning of fixed density conductive elements 518 at several vertices 503 located at the corner of a wound-filling matrix 501. In some implementations, a single fixed density conductive element 518 may be used for calibration. In some implementations, a calibration may be performed on an area having no conductive elements positioned therein.

Figure 5B:
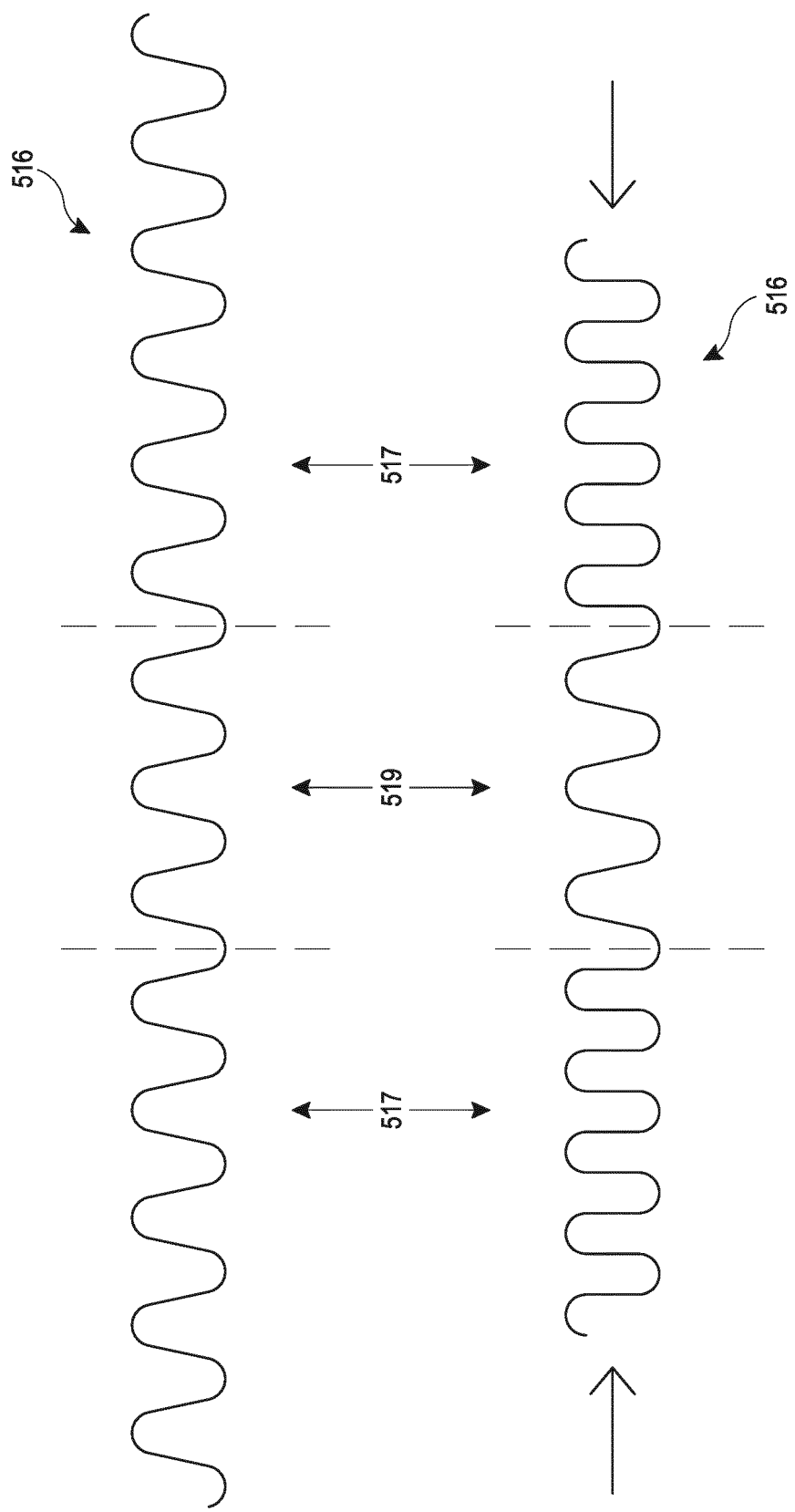

In some embodiments, the fixed density conductive element 518 may be a non-flexible (substantially rigid) conductive strip. The non-flexible conductive strip may be similar to the conductive strips 416 described elsewhere herein, except the non-flexible conductive strip or at least a portion of the length of the strip may be non-flexible such that the bends in the conductive wire neither collapse nor expand upon compression or extension of the medical device. The non-flexible conductive strip or non-flexible portion of the conductive strip may be made relatively rigid through any suitable means. For instance, the non-flexible strip may comprise a more rigid material than the flexible conductive strips 416 and/or may be made of a thicker gauge wire. The non-flexible conductive strip may be flanked on both ends by flexible members which absorb the strain of compression and/or expansion. For instance, the non-flexible conductive strip may be flanked by elastic fabric on either side and/or by flexible conductive strips 416, described elsewhere herein. The non-flexible conductive strips may be coupled to the medical device along lengths of the device expected to experience no or little dimensional changes or may be coupled to the device along lengths expected to be compressed or extended, particularly when the non-flexible conductive strip is flanked by flexible members. In some implementations, conductive strips 516 may comprise both flexible portions 517 and non-flexible portions 519, as schematically illustrated in FIG. 5B, showing the compression of a conductive strip 516 comprising both flexible portions 517 and non-flexible portions 519. For instance, there may be one or more non-flexible portions 517 positioned along the length of a conductive strip 516. In some implementations, the flexible portions 517 may be used to measure density changes, which may be correlated to wound closure, whereas the non-flexible portions 519 may be used for calibrating the detection device.

Detection of Dimensional Changes in the Medical Device

Figure 6:
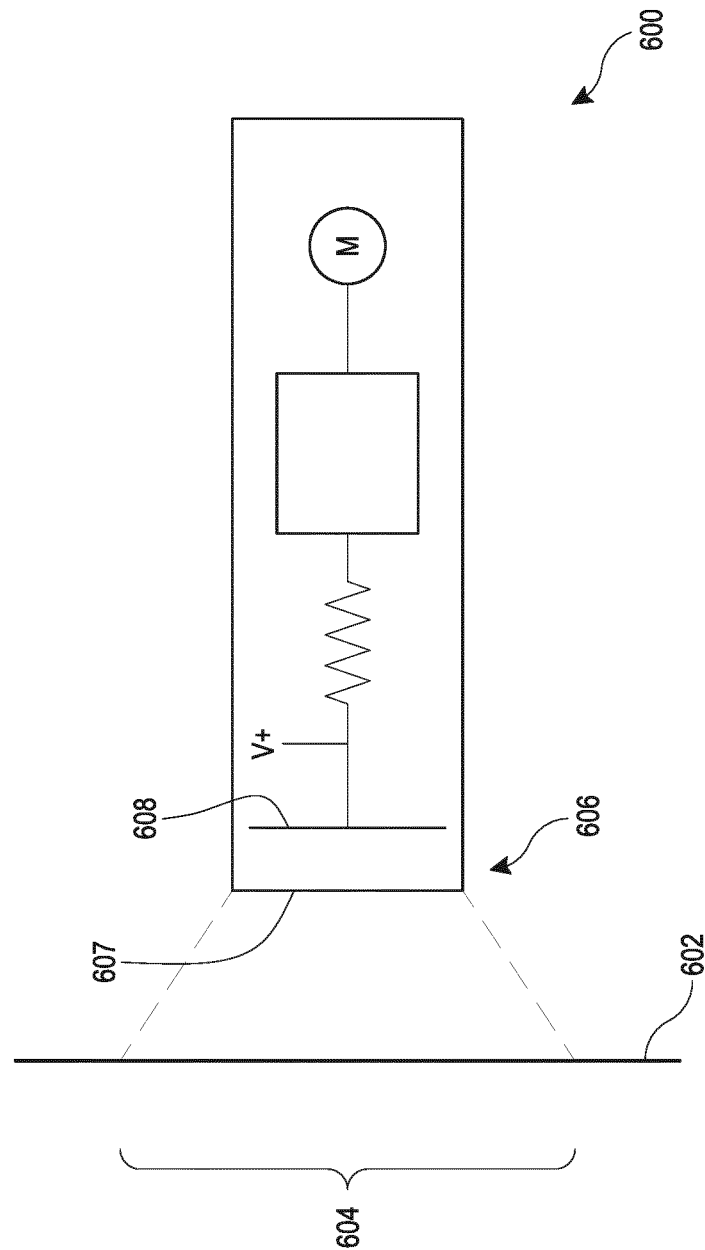
FIG. 6 schematically illustrates an example of a detection device comprising a capacitive plate according to some embodiments.

In some embodiments, the detection device may be configured as a non-contact device. FIG. 6 schematically illustrates an example of a detection device 600 positioned proximate to the surface 602 of a medical device, such as a wound filler. The detection device 600 may be configured as a scanning device, in which the device performs a detection measurement over an effective detection area 604. In some implementations, the device can be scanned over an area larger than the detection area 604, such that the detection area 604 is continually updated. The detection device 600 may be hand-held. The detection device 600 may comprise a distal end 606 configured to scan the detection area 604. The distal end 606 may comprise a relatively flat surface 607 configured to be placed over and proximate to the surface 602 of the medical device for detection. The detection device 600 can determine and provide indication of one or more dimensional changes, such as compression of a wound filler. Indication can be one or more of visual, audible, tactile, or the like.

In some embodiments, the detection device 600 may comprise one or more capacitive plates 608 positioned at the distal end 606. The one or more capacitive plates 608 may be oriented such that the faces of the plates 608 are parallel to the relatively flat surface 607. In some embodiments, the one or more capacitive plates 608 may be positioned just behind the flat surface 607 (for example, behind a non-conductive casing forming the flat surface 607), as shown in FIG. 6. In some embodiments, the one or more capacitive plates 608 may form the flat surface 607 or may be integral with the flat surface 607, such that the plates 608 are exposed or partially exposed. The capacitive plate 608 may be a capacitive element in a form other than a flat plate. The shape of the capacitive plate 608 may be used as is known in the art to modulate the zone of detection or detection volume. For instance, the shape may be used to establish a detection zone that extends substantially straight form the capacitive plate, a detection zone that extends as a cone (for example, a 90 degree cone) from the capacitive plate, or an omnidirectional detection zone (for example, a substantially spherical detection zone). In some implementations, the range of sensitivity may be modulated as is known in the art. The range of sensitivity may be used to limit the depth of detection as described elsewhere herein. For example, the range of sensitivity may be less than about 5 mm, less than about 6 mm, less than about 10 mm, less than about 15 mm, less than about 18 mm, less than about 20 mm, less than about 25 mm, less than about 30 mm, less than about 50 mm, or greater than or equal to about 50 mm. The detection device 600 may be configured to apply a voltage/current to the one or more capacitive plates 608. The amount of charge stored on a capacitive plate 608 may be modulated by the material properties of a detection volume adjacent the capacitive plate 608. The detection volume may be an indefinite volume, in which the closer to the capacitive plate 608 a material is positioned the larger its impact on the charge of the plate 608 (for example, a spherical volume centered around the capacitive plate 608). The dielectric constant of the detection volume, or an averaged dielectric constant, can influence the amount of charge stored on the one or more capacitive plates 608. The detection device 600 may comprise circuitry similar to that found in an electronic stud finder, such as that described in U.S. Pat. No. 4,099,118, titled "Electronic Wall Stud Sensor", issued Jul. 4, 1978, which is hereby incorporated by reference in its entirety. For instance, the detection device 600 may use the variable charge stored on the one or more capacitive plates 608 to modulate the time constant of a multi-vibrator or other timing component. The modulated time constant may be compared to a component with a fixed timing constant to determine a difference in the charge (e.g., via a meter M). The detection device 600 may output a voltage, current, or other electronic parameter (a reading) that is correlated to the charge on the one or more capacitive plates 608, affected by the variable dielectric constant of the detection area 604.

In some embodiments, the detection device 600 may be configured similar to that shown in FIG. 6 and as described elsewhere herein, but may use a radio transmitter and receiver alternatively to or in addition to capacitive plates for detection. The detection device 600 may use electromagnetic waves (for example, radio waves) in combination with a flexible conductive element 416 to assess the configuration, arrangement, and/or positioning of the medical device. The detection device 600 may comprise a radio transmitter for transmitting radio waves. The radio transmitter may transmit waves across a spectrum of detectable frequencies. The transmitted frequency may change over time. The radio transmitter may vary the frequency according to any suitable pattern. For example, the radio transmitter may continuously cycle between a minimum frequency and a maximum frequency. The frequency may be modulated by conductive, inductive, and/or capacitive circuit elements. The change in frequency over time may follow a preset time scale and/or may be adjusted by the user. In some implementations, the radio transmitter may transmit multiple frequencies simultaneously. The radio transmitter can be configured to direct the waves toward the medical device. The radio transmitter may comprise an aerial/antenna. The detection device 600 may comprise a radio receiver configured to detect electromagnetic waves. The radio receiver may be configured with circuitry to determine the frequency of the detected waves. The radio receiver may be configured to identify a wave from a plurality of waves comprising a maximum amplitude. The radio receiver may be configured to filter out electromagnetic noise. The radio receiver may be configured to register frequencies of waves above a threshold amplitude. In some implementations, the detection device 600 may be configured to produce a voltage and/or current measurement corresponding to the detected frequency value.

The flexible conductive element 416 may be used as a radiofrequency (RF) resonator (such as, an untuned aerial). The flexible conductive element 416 may receive and simultaneously transmit the received electromagnetic wave. The flexible conductive element 416 may experience a particular resonant frequency at which it resonates and transmits the received wave at a detectably higher amplitude than at other frequencies. The resonant frequency of the flexible conductive element 416 may be affected by the overall length, shape, and/or material properties of the flexible conductor element 416. In some embodiments, the flexible conductive element 416 will resonate better where it acts as a full wave, half-wave, quarter wave, or harmonic wave oscillator to an RF response. Expansion or compression of a flexible conductive element 416, as described elsewhere herein, may modulate the resonant frequency of the flexible conductive element 416 (for example, the wavelength of the resonant frequency may drop as a flexible conductive element 416, such as a zig-zag conductive element, is compressed). Altering the length of the resonator in the direction of the RF source can alter its resonant response. The detection device 600 may detect the resonant frequency of the flexible conductive element 416 by using the transmitter to transmit waves of various frequencies across a spectrum and using the receiver to identify at which frequency the flexible conductive element 416 resonates. The length of the resonator can be determined from the adsorption and/or transmission response of the resonator. The amount of compression or expansion of the flexible conductive element 416 can be determined according to one or more calibration techniques, described elsewhere herein.

In some embodiments, the resonator may be fixed. For example, a conductive element, such as the element 416, may be configured not to be compressed or extended. A capacitive element and/or inductive element may be coupled to the medical device. Dimensional changes in the medical device may alter the spatial positioning of the capacitive and/or inductive element relative to the resonator. The spatial positioning may modulate the tuning of the resonator so that the frequency at which it resonates depends on dimensional changes in the medical device, such as the amount of compression of a wound filler.

In some embodiments, the detection device 600 may be configured similar to that shown in FIG. 6 and as described elsewhere herein, but may generate a magnetic field. The magnetic field can be a low-power fluctuating magnetic field. Changes due to compression of the medical device, such as a wound filler, may alter (for example, raise) the magnetic permeability or permittivity within the detection area. For instance, changes in the resonant frequency of a flexible conductive element, such as a flexible conductive strip, may alter the magnetic permittivity of the detection area. The magnetic permittivity within a detection area may be detected using the magnetic field generated by the detection device 600.

The strategic positioning of conductive elements across the surface of the medical device can be used to effect changes in the dielectric constant of the detection volume of the one or more capacitive plates 608 of the detection device 600 upon compaction or expansion of the surface area of the medical device. In some embodiments, the strategic positioning of flexible conductive elements 416 may be used to effect changes in the resonant frequency detected by the detection device 600 upon compaction or expansion of the surface area of the medical device. The medical device may be configured to exhibit a changing dielectric constant primarily across a surface area of the medical device, depending on the device configuration at any point in time, and to maintain a relatively steady dielectric constant across the thickness or depth of the medical device. Therefore, the detection volume may be effectively treated as a detection area 604 across which changes in the dielectric constant are expected to occur. In certain embodiments, changes across the thickness of the medical device may alternatively or additionally be detected. The size of the effective detection area 604 across which changes in the dielectric constant and/or resonant frequency of the medical device can effectively be measured may depend on the electronic parameters of the detection device 600 (for example, the size of the capacitive plate 608, the configuration or number of capacitive plates 608, the voltage applied to the plate 608, the inclusion of amplifying circuitry, the calibration of the detection device 600, etc.). The compression or expansion of the medical device, or any other changes in the dimensions of the surface area of the medical device may result in an increase or decrease of the density of a single flexible conductive element 416 or the density of a plurality of discrete conductive elements 404 or conductive filler 402 within localized areas of the medical device. Density changes of the conductive elements within a detection area 604 of the detection device 600 may be detected by an increase or decrease in the localized dielectric constant which may modulate the amount of charge stored on the one or more capacitive plates 608 and/or by an increase or decrease in the resonant frequency detected by a radio receiver.

FIGS. 7A-7D schematically illustrate changes in density of conductive elements positioned within a detection area 700 of the detection device. FIG. 7A shows the isotropic compression of a medical device comprising discrete conductive elements 704. FIG. 7B shows the anisotropic compression of a medical device comprising discrete conductive elements 704. FIG. 7C shows the anisotropic compression of a medical device comprising conductive wires 714. FIG. 7D shows the anisotropic compression of a medical device comprising conductive strips 716. During compression of the medical device in each of these examples, the amount of conductive material within the effective detection area 700 (the density of conductive material) is increased, such that the effective dielectric constant of the medical device within the detection area 700 may be modulated (for example, increased by the higher density of conductive metal). During expansion of the medical device, the density of conductive material within the effective detection area 700 may be modulated in an opposite manner (for example, decreased).

In some embodiments, the detection device may be pre-calibrated. For instance, prior to clinical use the detection device may be used to make a plurality of measurements on different calibration standards. The calibration standards may comprise the same conductive elements used in the medical device, positioned at various arrangements that constitute various spatial densities of the conductive material. The spatial densities may be indicative of the range of spatial densities of the conductive elements expected to be measured during clinical use of the medical device. The calibration measurements may be correlated to distances between conductive elements (for example, along a single direction or over a two-dimensional area) or any other suitable measures that can reflect spatial changes experienced by the medical device. In some implementations, the calibration measurements can be used to create a standard curve and/or a look-up table, from which spatial measurements may be interpolated or extrapolated based on readings from the detection device. In some implementations, a mathematical expression can be defined relating the detection device readings to spatial measurements, such as by solving an analytic equation using calibration measurements to determine relevant parameters. In some implementations, the calibration measurements may be performed on the medical device comprising the actual conductive element to be used prior to implantation or attachment of the medical device to the body.

In some embodiments, the detection device may be entirely or partially calibrated during clinical use. For example, the clinician may scan an area of the medical device comprising a fixed density conductive element, as described elsewhere herein. This reading may be compared to one or more readings from areas comprising non-fixed conductive elements. For instance, the fixed density conductive element may provide a baseline reading. Readings from other areas may be expressed relative to the baseline reading. In this manner, relative compression and/or expansion of the device may be tracked over time. The detection device may be configured to read a calibration value and output a relative measurement or the clinician may manually record the reference value and calculate the variable density readings accordingly. In some implementations, the fixed density conductive element may be configured at a density approximate a final expected density. For instance, the density of the fixed density conductive element positioned in or on a wound filler may be indicative of the density that similar non-fixed conductive elements are expected to achieve near full compression or collapse of the wound filler (for example, when the wound is near closing) or at a point where the wound filler is expected to be swapped out. The variable readings of the conductive element may then approach the baseline reading as the wound closing procedure progresses. Using such methods, the detection device can be configured to provide measurements of wound closure without requiring pre-calibration or even storage of calibration values. In some embodiments, the user may perform a relatively concurrent calibration measurement using a calibration standard that is not incorporated into the medical device. In some embodiments, the relative difference in readings between the fixed density conductive element and the conductive element may be correlated to a change in spatial dimensions using a calibration curve, table, or equation.

In some embodiments, the user may be able to calibrate the detection device by "zeroing" a reading, in which the measured value is effectively set to zero. Zeroing a reading may adjust the detection range of the detection device to more effectively detect and distinguish values within a range of interest (for example, ranges corresponding to the different spatial densities of conductive elements experienced by the medical device in clinical use). The detection device may zero a reading, for example, by using a potentiometer to adjust the voltage and/or current applied to the one or more capacitive plates or to affect other components of the circuitry. In some implementations, a detection area comprising no conductive elements (for example, a portion of a wound filler without any conduction elements) may be used to zero the detection device. This calibration may be used in conjunction with other calibration procedures described herein. In some implementations, a detection area comprising a fixed density conduction element may be used to zero the device.

In some embodiments, the system may include a processor and/or memory. In some embodiments, the processor and/or memory are internal components of the detection device. In some embodiments, the detection device is operatively coupled to an external processor and/or external memory, such as a computer, tablet, smart phone, etc. The detection device may be wirelessly coupled (for example, using WIFI, Bluetooth, etc.) to the external components. The detection device may be coupled using a data cord (for example, a USB cable). The detection device may be configured to store calibration values or other calibration data.

The detection device may be configured to determine a metric of spatial density, movement, reconfiguration, etc. For example, the detection device may be configured to determine a metric of wound closure (for example, a closure distance or a reduction in area). The detection device may include a display for displaying raw readings and/or determined metrics. The detection device may include input features for a user to set operating parameters. In some embodiments, the user may be able to select a calibration mode such that the reading is used as a reference reading and/or a zero reading, as described elsewhere herein. For instance, the detection device may include a button the user presses when making a calibration reading. In some embodiments, the detection device may provide continually updated readings. For instance, the detection device may be moved (for example, in a linear fashion) across a detection path while refreshing the reading to correspond to the changing detection area. The detection device may refresh according to a predetermined time increment. During the time increment the detection device may average the input from the detection device to determine an output value. In some embodiments, the detection device may include a capture button wherein the user can request the detection device make a measurement at the moment the button is pressed.

In some embodiments, the detection device may be configured as a sensor to be attached to the body (for example, over the medical device) for an indefinite period of time. The sensor may be configured to simultaneously and/or sequentially scan one or more detection areas, which may be strategically positioned over the medical device. The sensor may be strapped, adhered (for example, adhesive), or coupled to the body by any suitable means. For example, the sensor may be configured in a patch or wrist-watch type configuration. The sensor may be in contact with the medical device or coupled such that there is a gap or space between the sensor and the medical device.

Wound Treatment

Figure 8:
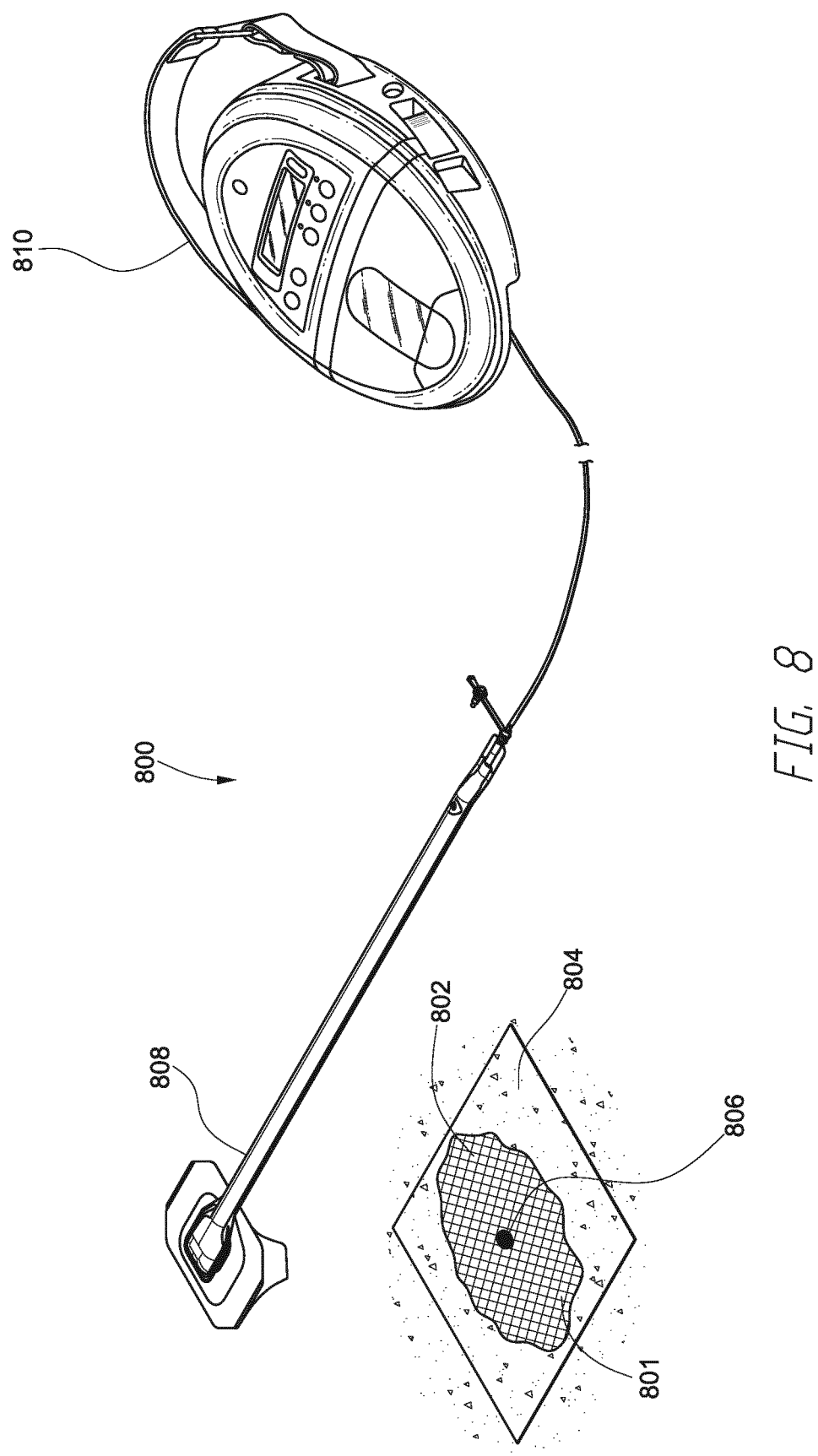
FIG. 8 illustrates a negative pressure treatment system applied to a wound filler inserted into a wound according to some embodiments.

In some embodiments, the medical device is a wound-closure device, such as a wound filler (for example, a wound-filling matrix), as described elsewhere herein. In some implementations, such devices may be used in combination with negative pressure to treat the wound and promote wound closure. FIG. 8 illustrates an embodiment of a negative pressure treatment system 800 that comprises a wound filler 802 inserted into a wound 801. The wound filler 802 may comprise porous materials such as foam, and in some embodiments may comprise one or more embodiments of wound closure devices described elsewhere herein. In some embodiments, the perimeter or top of any wound closure device inserted into the wound 801 may also be covered with foam or other porous materials. A single drape 804 or multiple drapes may be placed over the wound 801, and is preferably adhered or sealed to the skin on the periphery of the wound 801 so as to create a fluid-tight seal. An aperture 806 may be made through the drape 804 which can be manually made or preformed into the drape 804 so as to provide a fluidic connection from the wound 801 to a source of negative pressure such as a pump 810. Preferably, the fluidic connection between the aperture 106 and the pump 810 is made via a conduit 808. In some embodiments, the conduit 808 may comprise a RENASYS® Soft Port™, manufactured by Smith & Nephew. Of course, in some embodiments, the drape 804 may not necessarily comprise an aperture 806, and the fluidic connection to the pump 810 may be made by placing the conduit 808 below the drape. In some wounds, particularly larger wounds, multiple conduits 808 may be used, fluidically connected via one or more apertures 806.

In some embodiments, the drape 804 may be provided with one or more corrugations or folds. Preferably, the corrugations are aligned along the longitudinal axis of the wound, and as such may support closure of the wound by preferentially collapsing in a direction perpendicular to the longitudinal axis of the wound. Such corrugations may aid in the application of contractile forces parallel to the wound surface and in the direction of wound closure. Examples of such drapes may be found in application Ser. No. 12/922, 118, titled "Vacuum Closure Device," filed Nov. 17, 2010 (published as US 2011/0054365), which is hereby incorporated by reference in its entirety.

In use, the wound 801 is prepared and cleaned. In some cases, such as abdominal wounds, a non- or minimally-adherent organ protection layer (not illustrated) may be applied over any exposed viscera. The wound filler 802 is then inserted into the wound, and is covered with the drape 804 so as to form a fluid-tight seal. A first end of the conduit 808 is then placed in fluidic communication with the wound, for example via the aperture 806. The second end of the conduit 808 is connected to the pump 810. The pump 810 may then be activated so as to supply negative pressure to the wound 801 and evacuate wound exudate from the wound 801. Negative pressure may also aid in promoting closure of the wound 801, for example, by approximating opposing wound margins. The systems, devices, and methods disclosed herein may be used in combination with a wound closure treatment or similar treatments to monitor the progression of the wound closure, by assessing the collapse of the wound filler 802.

Although this disclosure describes certain embodiments, it will be understood by those skilled in the art that many aspects of the methods and devices shown and described in the present disclosure may be differently combined and/or modified to form still further embodiments or acceptable examples. All such modifications and variations are intended to be included herein within the scope of this disclosure. Indeed, a wide variety of designs and approaches are possible and are within the scope of this disclosure. No feature, structure, or step disclosed herein is essential or indispensable. Moreover, while illustrative embodiments have been described herein, the scope of any and all embodiments having equivalent elements, modifications, omissions, combinations (for example, of aspects across various embodiments), substitutions, adaptations and/or alterations as would be appreciated by those in the art based on the present disclosure. While certain embodiments have been described, these embodiments have been presented by way of example only, and are not intended to limit the scope of protection.

Features, materials, characteristics, or groups described in conjunction with a particular aspect, embodiment, or example are to be understood to be applicable to any other aspect, embodiment or example described in this section or elsewhere in this specification unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

Furthermore, certain features that are described in this disclosure in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations, one or more features from a claimed combination can, in some cases, be excised from the combination, and the combination may be claimed as a subcombination or variation of a subcombination.

Moreover, while operations may be depicted in the drawings or described in the specification in a particular order, such operations need not be performed in the particular order shown or in sequential order, or that all operations be performed, to achieve desirable results. Other operations that are not depicted or described can be incorporated in the example methods and processes. For example, one or more additional operations can be performed before, after, simultaneously, or between any of the described operations. Further, the operations may be rearranged or reordered in other implementations. Those skilled in the art will appreciate that in some embodiments, the actual steps taken in the processes illustrated and/or disclosed may differ from those shown in the figures. Depending on the embodiment, certain of the steps described above may be removed, others may be added. Furthermore, the features and attributes of the specific embodiments disclosed above may be combined in different ways to form additional embodiments, all of which fall within the scope of the present disclosure. Also, the separation of various system components in the implementations described above should not be understood as requiring such separation in all implementations, and it should be understood that the described components and systems can generally be integrated together in a single product or packaged into multiple products.

For purposes of this disclosure, certain aspects, advantages, and novel features are described herein. Not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Conditional language, such as "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without user input or prompting, whether these features, elements, and/or steps are included or are to be performed in any particular embodiment.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain embodiments, the terms "generally parallel" and "substantially parallel" refer to a value, amount, or characteristic that departs from exactly parallel by less than or equal to 15 degrees, 10 degrees, 5 degrees, 3 degrees, 1 degree, 0.1 degree, or otherwise.

The scope of the present disclosure is not intended to be limited by the specific disclosures of preferred embodiments in this section or elsewhere in this specification, and may be defined by claims as presented in this section or elsewhere in this specification or as presented in the future. The language of the claims is to be interpreted broadly based on the language employed in the claims and not limited to the examples described in the present specification or during the prosecution of the application, which examples are to be construed as non-exclusive.

What is claimed is:

1. A wound therapy system comprising:
   a wound filler configured to be at least partially inserted into a wound;
   a conductive element coupled to the wound filler, wherein a density of the conductive element increases within a detection area of the wound filler upon compression of the wound filler; and
   a detection device configured to assess a degree of wound closure based on a measurement of the density of the conductive element in the detection area, wherein the density is dependent on the amount of compression of the wound filler,
   wherein the measurement comprises a measurement of the dielectric constant of the detection area of the wound filler, and wherein the dielectric constant changes based on a compression of the conductive element as a result of the compression of the wound filler.

2. The system of claim 1, wherein the conductive element comprises a conductive filler embedded at least in the detection area of the wound filler.

3. The system of claim 1, wherein the conductive element comprises a plurality of conductive elements spaced across at least the detection area of the wound filler.

4. The system of claim 1, wherein:
the wound filler is configured to be compressed in a first direction and not substantially compressed in a second direction, the second direction being perpendicular to the first direction;
the conductive element comprises a plurality of conductive wires, each conductive wire comprising a length extending from a first end to a second end; and
the conductive wires are arranged substantially parallel to one another and so that the lengths of the conductive wires extend along the second direction.

5. The system of claim 1, wherein the conductive element comprises a substantially flexible conductive element.

6. The system of claim 5, wherein the substantially flexible conductive element comprises a conductive strip having a width defining a lateral dimension and a length defining a longitudinal dimension, the conductive strip comprising a conductive wire including a plurality of bends spaced across the length of the conductive strip, wherein at least some of the bends are configured to allow the conductive strip to be compressed or extended along the longitudinal direction such that the density of the conductive wire is increased or decreased along at least a portion of the longitudinal dimension.

7. The system of claim 6, wherein the measurement comprises a measurement associated with the resonant frequency of the flexible conductive element.

8. The system of claim 6, wherein the plurality of bends forms a sinusoidal, serpentine, and/or triangular pattern.

9. The system of claim 1, wherein one or more fixed density conductive elements are coupled to the wound filler, and wherein the density of the one or more fixed density conductive elements does not substantially change upon compression of the wound filler.

10. The system of claim 9, wherein the detection device is configured to be calibrated based on the measurement of a detection area comprising the fixed density conductive element.

11. The system of claim 1, further comprising a negative pressure source configured to provide negative pressure to a wound, the negative pressure source configured to be in fluid communication with the wound filler.

12. A method for assessing a degree of wound closure of a wound, the method comprising:
placing a detection device in proximity of a detection area of a wound filler, the wound filler at least partially inserted into the wound, the wound filler comprising a conductive element coupled to the wound filler, wherein a density of the conductive element increases within the detection area of the wound filler upon compression of the wound filler; and
using the detection device to make a measurement based on the density of the conductive element in the detection area, wherein the density is dependent on the amount of compression of the wound filler.

13. The method of claim 12, further comprising calibrating the detection device by using the detection device to take a calibration measurement over an area of the wound filler comprising a fixed density conductive element, wherein a density of the fixed density conductive element does not change upon compression of the wound filler.

14. The method of claim 12, further comprising relating the measurement to a degree or amount of wound closure.

15. A method for assessing a degree of wound closure of a wound, the method comprising, by a detection device:
making a measurement within a detection area of a wound filler at least partially inserted into the wound, the wound filler comprising a conductive element coupled to the wound filler, wherein a density of the conductive element increases within the detection area of the wound filler upon compression of the wound filler comprising the detection area; and
based on the measurement, indicating a degree of compression of the wound filler.

16. The method of claim 15, wherein making the measurement comprises applying a voltage to one or more capacitive plates within the detection device, wherein the amount of charge stored on the one or more capacitive plates is configured to be modulated by a dielectric constant of the detection area, and wherein the measurement is reflective of the amount of charge stored on the one or more capacitive plates.

17. The method of claim 15,
wherein the conductive element is a flexible conductive strip having a width defining a lateral dimension and a length defining a longitudinal dimension, the flexible conductive strip comprising a conductive wire comprising a plurality of bends spaced across the length of the flexible conductive strip, wherein at least some of the bends are configured to allow the flexible conductive strip to be compressed or extended along the longitudinal direction such that the density of the conductive wire is increased or decreased along at least a portion of the length of the flexible conductive strip; and
wherein making the measurement comprises transmitting a radio wave toward the flexible conductive strip, receiving a radio wave transmitted from the direction of the flexible conductive strip, and measuring the resonant frequency of the flexible conductive strip, the resonant frequency being dependent upon the degree of compression experienced by the flexible conductive strip.

* * * * *